US009999646B2

(12) United States Patent
Lee et al.

(10) Patent No.: US 9,999,646 B2
(45) Date of Patent: Jun. 19, 2018

(54) METHOD OF TREATING INFLAMMATION, ALLERGY AND ASTHMA WITH A PURIFIED EXTRACT (ATC1) ISOLATED FROM *PSEUDOLYSIMACHION ROTUNDUM* VAR. *SUBINTEGRUM* CONTAINING ABUNDANT AMOUNT OF ACTIVE INGREDIENT

(71) Applicants: YUNGJIN PHARMACEUTICAL CO., LTD, Seoul (KR); KOREA RESEARCH INSTITUTE OF BIOSCIENCE AND BIOTECHNOLOGY, Daejeon (KR)

(72) Inventors: Yongnam Lee, Suwon-si (KR); Ji-seok Yoo, Suwon-si (KR); Dae-hee Shin, Seoul (KR); Byung-hwan Ryoo, Seongnam-si (KR); Sei-ryang Oh, Daejeon (KR); Kyung-seop Ahn, Daejeon (KR); Hyeongkyu Lee, Daejeon (KR); Ok-kyoung Kwon, Daejeon (KR); Doo-young Kim, Daejeon (KR); Jung-hee Kim, Daejeon (KR); Hyuk-hwan Song, Daejeon (KR)

(73) Assignees: YUNGJIN PHARMACEUTICAL CO., LTD, Seoul (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 103 days.

(21) Appl. No.: 15/261,999

(22) Filed: Sep. 11, 2016

(65) Prior Publication Data
US 2017/0049838 A1 Feb. 23, 2017

Related U.S. Application Data

(62) Division of application No. 14/653,852, filed as application No. PCT/KR2013/011986 on Dec. 23, 2013, now Pat. No. 9,592,263.

(30) Foreign Application Priority Data

Dec. 31, 2012 (KR) .......................... 10-2012-0158130
Jul. 17, 2013 (KR) .......................... 10-2013-0084167

(51) Int. Cl.
A61K 36/00 (2006.01)
A61K 36/80 (2006.01)
A61K 31/7048 (2006.01)
A61K 31/192 (2006.01)
A61K 9/00 (2006.01)
A61K 47/24 (2006.01)
A61K 9/08 (2006.01)
A61K 47/36 (2006.01)
A61K 9/16 (2006.01)
A61K 9/20 (2006.01)
A61K 9/48 (2006.01)
A23L 33/105 (2016.01)

(52) U.S. Cl.
CPC ............ *A61K 36/80* (2013.01); *A23L 33/105* (2016.08); *A61K 9/00* (2013.01); *A61K 9/0019* (2013.01); *A61K 9/0078* (2013.01); *A61K 9/08* (2013.01); *A61K 9/1652* (2013.01); *A61K 9/2018* (2013.01); *A61K 9/4858* (2013.01); *A61K 31/192* (2013.01); *A61K 31/7048* (2013.01); *A61K 47/24* (2013.01); *A61K 47/36* (2013.01); *A61K 2236/33* (2013.01); *A61K 2236/55* (2013.01)

(58) Field of Classification Search
CPC ..................................................... A61K 36/00
See application file for complete search history.

(56) References Cited

U.S. PATENT DOCUMENTS

2012/0183632 A1    7/2012 Lee et al.

FOREIGN PATENT DOCUMENTS

| KR | 10-2006-0125489 | 12/2006 |
| KR | 10-0860080 | 9/2008 |
| KR | 10-2013-0084167 | 12/2014 |
| KR | 10-1476045 | 12/2014 |
| KR | 10-2014-0136790 | 3/2015 |
| KR | 10-1504651 | 3/2015 |

OTHER PUBLICATIONS

Written Opinion, PCT/KR2013/011986, 6 Pages.
International Search Report, PCT/KR2013/011986, 4 Pages.
Pawankar, R., 2001, Mast cells as orchestrators of the allergic reaction: the IgE-IgE receptor mas cell network, Current Opinion in Allergy and Clinical Immunology, 1: 3-6.
Park, EJ., et al., 2009, Liquid chromatography-mass spectrometry for the simultaneous determination of the catalpol-related iridoid glucosides, verproside, isovanilloylcatalpol, catalposide and 6-O-veratroyl catapol in rat plasma, Biomed. Chroma., 23: 980-986.
Kim, DY., Analysis of iridoids from *Pseudolysimachion* genus in Korea, Feb. 2007, 47 pages.

(Continued)

*Primary Examiner* — Qiuwen Mi
(74) *Attorney, Agent, or Firm* — Kirk Hahn

(57) ABSTRACT

The present invention relates to inventive novel industrialized method for preparing purified extract containing more abundant active ingredients such as catalpol derivatives from the extract of *Pseudolysimachion rotundum* var *subintegrum* than that prepared by the conventional preparation method disclosed in the prior art and the therapeutics or functional health food comprising the purified extract for treating and preventing inflammatory, allergic or asthmatic disease. The purified extract showed more potent anti-inflammatory, anti-allergy and anti-asthma activity than that prepared by the conventional preparation method disclosed in the prior art through various in vivo tests such as inhibition test on the reproduction of eosinophil, the release of immunoglobulin and inflammatory chemokines in plasma and bronchoalveolar fluid as well as the suppression of airway hyperresponsiveness and goblet cell hyperplasia in a OVA-sensitized/challenged mouse model.

4 Claims, 15 Drawing Sheets

(56) References Cited

OTHER PUBLICATIONS

Chen, M. et al., 2011, The effects of tripolide on airway remodelling and transforming growth factor-B1/Smad signalling pathway in ovalbulin-sensitized mice, Immunol., 132: 376-384.

Maggi, E., 1998, The TH1/TH2 paradigm in allergy, Immunotech., 3, 233-244.

Elias, JA, et al., 2003, New insights into the pathogenesis of asthma, J. Clin. Invest., 111, 291-297.

Kwak, YG., et al., 2003, Involvement of PTEN in airway hyper-responsiveness and inflammation in bronchial asthma, J. Clin. Invest., 111:7, 1083-1092.

Lee, KS., et al., 2006, Inhibition of phosphoinositide 3-kinase delta attentuates allergic airway inflammation and hyperresponsiveness in murine asthma model, FASEB J., 20, 455-465.

Renz, H., et al., 1993, T cells expressing specific Vbeta elements regulate imunnoglobulin E production and airways responsiveness in vivo, J. Exp. Med., 177, 1175-1180.

2012 International Symposium and Annul Meeting of the KSABC, 227 pages.

Kay, A.B., 2001, Allergy and Allergic Diseases, N.E.J. Med., 344, 3037.

Minoguchi, K. et al., 1999, Pathophysiology of asthma, Chap 8, 97-104.

Barnes, PJ et al., 1998, Inflammatory mediators of asthma: an update, Pharma. Rev., 50:4, 515-596.

METHOD OF TREATING INFLAMMATION, ALLERGY AND ASTHMA WITH A PURIFIED EXTRACT (ATC1) ISOLATED FROM *PSEUDOLYSIMACHION ROTUNDUM* VAR. *SUBINTEGRUM* CONTAINING ABUNDANT AMOUNT OF ACTIVE INGREDIENT

This application is a Division of and claims priority upon U.S. application Ser. No. 14/653,852 filed on Jun. 19, 2015 (pending), which is a U.S. National Phase Patent Application under 35 U.S.C. § 371 of International Application PCT/KR2013/011986, filed on Dec. 23, 2013, which claims priority to Korean Patent Application No. 10-2013-0084167, filed on Jul. 17, 2013 and Korean Patent Application No. 10-2012-0158130, filed on Dec. 31, 2012. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a purified extract isolated from *Pseudolysimachion rotundum* var. *subintegrum* containing abundant amount of active ingredient, the preparation thereof, and the composition comprising the same as an active ingredient for preventing or treating inflammation, allergy and asthma.

BACKGROUND ART

Generally, an inflammatory response is a normal response of human body associated with an edema, a pain etc in case that a tissue or a cell received any invasion causing some organic change in the tissue or cell. Recently, various kinds of cytokines have been found to be involved in the inflammatory disease.

Allergic reaction may be classified into four categories, i.e., type I, II, III and IV according to the types of response or two categories, i.e., immediate type allergic reaction such as type I, II or III, and delayed type allergic reaction such as type IV according to the types of the period from the re-sensitization time caused by allergen to the onset time of reaction.

Among them, type I allergy, being involved in IgE antibody and called as anaphylaxis type allergy, causes to a bronchial asthma, atopic diseases such as dermatitis or gastroenteritis etc, allergic rhinitis such as pollenosis, allergic conjunctivitis, food allergy and the like.

Asthma is regarded as a complex syndrome of the airways that is characterized by various clinical symptoms, for example, cough, dyspnea caused by airflow obstruction, acute or chronic airway inflammation, airway hyperresponsiveness (AHR) and structural remodeling and can be reversibly or irreversibly recoverable. Most of asthma is allergic disease and is characterized by chronic airway inflammation and bronchial hyperresponsiveness (Minoguchi K and Adachi M., Pathophysiology of asthma. In: Cherniack N S, Altose M D, Homma I. editors. *Rehabilitation of the patient with respiratory disease*. New York: McGraw-Hill, 1999, pp 97-104).

The asthma can be classified two types, i.e., extrinsic asthma and intrinsic asthma. The extrinsic asthma is caused by exposing antigen and it is shown positive reaction in skin test or bronchial provocation test against the antigen. Usually causing ages is getting younger. It is mainly caused by House Dust Mite *Dermatophagoides* and pollen, epithelium of animal, fungi and so on. The intrinsic asthma is caused by upper respiratory infections, exercise, emotional instability, changing of climate of humidity and it is common to adult patient. Also, the IgE antigen of extrinsic asthma can be detected by skin test due to increasing IgE in serum.

With regards to pathophysiology, asthma is recognized by T-helper2 (Th2)-cell-driven chronic inflammation, and a variety of inflammatory mediators, such as cytokines, chemokines, signaling molecules, adhesion molecules and growth factors, from immune cells and structural cells in the airways are involved in various stages of asthma (Elias J A et al., *J Clin Invest.*, 111, pp 291-7, 2003). The activated inflammatory cells such as eosinophil, mast cells, alveolar macrophage etc in the bronchus of patients suffering from asthma, release various inflammatory mediators such as cystein leukotrienes, prostaglandins etc and is involved in potent bronchial constriction (Maggi E., Immunotechnology 3, pp 233-244, 1998; Pawankar R. Curr. Opin. Allergy Clin. Immunol., 1, pp 3-6, 2001; Barnes P J et al., Pharmacol. Rev. 50, pp 515-596, 1998).

Accordingly, since the reproduction of various cytokines involved in inflammatory cell activation, such as IL-4, IL-5, IL-13 etc and IgE and reproduction of cystein leukotrienes released from the inflammatory cells are the main causes of inflammation, allergic reaction and asthma, there have been much studied to develop the inhibiting agents from the reproduction of those till now.

The present inventors have been focused to develop potent treating agent derived from natural resources with safety and efficacy such as plant, animals etc having potent inhibiting activity from the reproduction of inflammatory cells and finally, have found that the extract of *Pseudolysimachion longifolium* showed potent anti-inflammatory, anti-allergy and anti-asthma activity (Korean Patent No. 10-860080) and various compounds isolated therefrom such as, verproside (6-O-3,4-dihydroxybenzoyl catalpol), picroside II (6-O-4-hydroxy-3-methoxybenzoyl catalpol), verminoside (6-O-3,4-Dihydroxy cinnamoyl catalpol), 6-O-veratroyl catalpol (6-O-3,4-Dimethoxy benzoyl catalpol), minecoside (6-O-3-hydroxy-4-methoxycinnamoyl catalpol), catalpol and the like, also showed potent anti-inflammatory, anti-allergy and anti-asthma activity (Korean Patent Publication No. 10-2006-125499).

However, there have been difficulties in mass-production and industrialization using by the extract of *Pseudolysimachion longifolium* since the plant extract contains very little active ingredients such as catalopol derivatives.

*Pseudolysimachion rotundum* var *subintegrum*, is a perennial herb distributed in Korea, China, Japan, Ostrov Sakhalin, and Russia.

Based on the previous studies on the anti-inflammatory, anti-allergy and anti-asthma activity of the extract of *Pseudolysimachion longifolium* disclosed in Korean Patent No. 10-860080, the present inventors have tried to develop more efficient method for preparing more potent and more abundant ingredients showing anti-inflammatory, anti-allergy and anti-asthma activity isolated from the extract of *Pseudolysimachion rotundum* var *subintegrum*.

However, there has been not reported or disclosed about the efficient method for preparing more potent and more abundant ingredients showing anti-inflammatory, anti-allergy and anti-asthma activity isolated from the extract of *Pseudolysimachion rotundum* var *subintegrum* than those in the above cited literatures, the disclosures of which are incorporated herein by reference.

Accordingly, the present inventors have found the novel industrialized method for preparing purified extract containing more abundant active ingredients such as catalpol derivatives from the extract of *Pseudolysimachion rotundum* var *subintegrum* and the purified extract showed more potent anti-inflammatory, anti-allergy and anti-asthma activity than that prepared by the conventional preparation method disclosed in the prior art through various in vivo tests such as inhibition test on the reproduction of eosinolphil, the release of immunoglobulin and inflammatory chemokines in plasma and bronchoalveolar fluid as well as the suppression of airway hyperresponsiveness and golblet cell hyperplasia in a OVA-sensitized/challenged mouse model.

DISCLOSURE

Technical Problem

The present invention provides a novel method for preparing purified extract containing abundant active ingredients such as catalpol derivatives from *Pseudolysimachion rotundum* var *subintegrum* and the extract prepared thereby.

The present invention also provides a pharmaceutical composition and a health food comprising the purified extract containing abundant active ingredients such as catalpol derivatives from *Pseudolysimachion rotundum* var *subintegrum* as an active ingredient in an effective amount to treat and prevent inflammatory, allergic or asthmatic disease.

The present invention also provides a use of a purified extract containing abundant active ingredients such as catalpol derivatives from *Pseudolysimachion rotundum* var *subintegrum* showing anti-inflammatory, anti-allergic and anti-asthmatic activity.

The present invention also provides a method of treating or preventing inflammatory, allergic or asthmatic disease in a mammal comprising administering to said mammal an effective amount of purified extract containing abundant active ingredients such as catalpol derivatives from *Pseudolysimachion rotundum* var *subintegrum*, together with a pharmaceutically acceptable carrier thereof.

Technical Solution

Accordingly, it is an object of the present invention to provide novel purified extract containing abundant catalpol derivatives from the extract of *Pseudolysimachion rotundum* var *subintegrum*.

The term "catalpol derivatives" disclosed herein comprises verproside, catalposide, picroside II, isovanilloyl catalpol and 6-O-veratroyl catalpol etc.

The term "*Pseudolysimachion rotundum* var *subintegrum*" disclosed herein comprises the cultivated or naturally grown plant and commercially available plant, but not intent to limit thereto herein.

The term "novel purified extract" disclosed herein comprises (a) the purified extract fractionated with butanol (designated as "ATC1" hereinafter) and (b) the purified extract with the secondary fractionation (designated as "ATC2" hereinafter).

Specifically, the term "the purified extract fractionated with butanol (ATC1)" is characterized by containing 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol based on the weight of total extract (100%) of *Pseudolysimachion rotundum* var *subintegrum*; preferably, 20-25% (w/w) verproside, 0.5-5% (w/w) veratric acid, 1-5% (w/w) catalposide, 0.5-5% (w/w) picroside II, 0.5-5% (w/w) isovanilloyl catalpol and 1-5% (w/w) 6-O-veratroyl catalpol based on the weight of total extract (100%) of *Pseudolysimachion rotundum* var *subintegrum*; or characterized by containing 12.3-47% (w/w) catalposide derivatives in total extract (100%) of *Pseudolysimachion rotundum* var *subintegrum* and having the relative mixed ratio (w/w) between the weight of each catalposide derivative, of 15.0-18.0 (w/w) verproside, 2.10-2.60 (w/w) catalposide, 1 (w/w) picroside II, 1.00-1.30 (w/w) isovanilloyl catalpol and 2.00-2.30 (w/w) 6-O-veratroyl catalpol; preferably, 16.0-17.0 (w/w) verproside, 2.20-2.50 (w/w) catalposide, 1 (w/w) picroside II, 1.10-1.20 (w/w) isovanilloyl catalpol and 2.10-2.20 (w/w) 6-O-veratroyl catalpol; more preferably, 16.20-16.99 (w/w) verproside, 2.40-2.45 (w/w) catalposide, 1 (w/w) picroside II, 1.10-1.19 (w/w) isovanilloyl catalpol and 2.10-2.19 (w/w) 6-O-veratroyl catalpol.

More specifically, the term "the purified extract fractionated with butanol (ATC1)" is characterized by being prepared by the process of; adding at least one extracting solvent selected from water, C1-C4 lower alcohol such as methanol, ethanol, butanol etc or the mixtures thereof, preferably, mixture of water and ethanol, more preferably, 30-80 (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; and adding about 0.5-20 fold volume (v/v), preferably, about 1-10 fold volume (v/v) of butanol, fractionating into water layer and butanol layer and collecting the butanol layer to afford the purified extract fractionated with butanol (ATC1) containing 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol based on the weight of total extract (100%) of *Pseudolysimachion rotundum* var *subintegrum* to treat and prevent inflammatory, allergic or asthmatic disease.

Accordingly, in an another embodiment of the present invention, the present invention also provides a method for preparing the purified extract fractionated with butanol (ATC1) isolated from *Pseudolysimachion rotundum* var *subintegrum* comprising the steps of; adding at least one extracting solvent selected from water, C1-C4 lower alcohol such as methanol, ethanol, butanol etc or the mixtures thereof, preferably, mixture of water and ethanol, more preferably, 30-80 (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; and adding about 0.5-20 fold volume (v/v), preferably, about 1-10 fold volume (v/v) of butanol, fractionating into water layer and butanol layer and collecting the butanol layer to afford the purified extract fractionated with butanol (ATC1) containing 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol based on the weight of total extract (100%) of *Pseudolysimachion rotundum* var *subintegrum* to treat and prevent inflammatory, allergic or asthmatic disease.

Specifically, the term "the purified extract with the secondary fractionation (ATC2)" is characterized by containing 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum*; preferably, 40-50% (w/w) verproside, 1-5% (w/w) veratric acid, 3-10% (w/w) catalposide, 2-5% (w/w) picroside II, 2-8% (w/w) isovanilloyl catalpol and 3-8% (w/w) 6-O-veratroyl catalpol based on the weight of total extract (100%) of *Pseudolysimachion rotundum* var *subintegrum*; or characterized by containing 36.5-91% (w/w) catalposide derivatives in total extract (100%) of *Pseudolysimachion rotundum* var *subintegrum* and having the relative mixed ratio (w/w) between the weight of each catalposide derivative, of 13.0-16.0 (w/w) verproside, 2.20-2.50 (w/w) catalposide, 1 (w/w) picroside II, 1.10-1.40 (w/w) isovanilloyl catalpol and 2.00-2.20 (w/w) 6-O-veratroyl catalpol; preferably, 14.0-15.0 (w/w) verproside, 2.30-2.45 (w/w) catalposide, 1 (w/w) picroside II, 1.20-1.35 (w/w) isovanilloyl catalpol and 2.00-2.10 (w/w) 6-O-veratroyl catalpol; more preferably, 14.50-14.99 (w/w) verproside, 2.35-2.43 (w/w) catalposide, 1 (w/w) picroside II, 1.25-1.34 (w/w) isovanilloyl catalpol and 2.01-2.09 (w/w) 6-O-veratroyl catalpol.

More specifically, the term "the purified extract with the secondary fractionation (ATC2)" is characterized by being prepared by the process of adding at least one extracting solvent selected from water, C1-C4 lower alcohol such as methanol, ethanol, butanol etc or the mixtures thereof, preferably, mixture of water and ethanol, more preferably, 30-80 (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; adding about 0.5-20 fold volume (v/v), preferably, about 1-10 fold volume (v/v) of butanol, fractionating into water layer and butanol layer and collecting the butanol layer to afford the purified extract fractionated with butanol (ATC1) at the 3rd step; and subjecting the purified extract fractionated with butanol (ATC1) to at least one purification process selected from the group consisting of reverse phase partition chromatography, normal phase partition chromatography, ion exchange chromatography, and size exclusion chromatography to afford the purified extract with the secondary fractionation (ATC2) containing 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum* to treat and prevent inflammatory, allergic or asthmatic disease.

Accordingly, in an another embodiment of the present invention, the present invention also provides a method for preparing the purified extract with the secondary fractionation (ATC2) isolated from *Pseudolysimachion rotundum* var *subintegrum* comprising the steps of; adding at least one extracting solvent selected from water, C1-C4 lower alcohol such as methanol, ethanol, butanol etc or the mixtures thereof, preferably, mixture of water and ethanol, more preferably, 30-80 (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; adding about 0.5-20 fold volume (v/v), preferably, about 1-10 fold volume (v/v) of butanol, fractionating into water layer and butanol layer and collecting the butanol layer to afford the purified extract fractionated with butanol (ATC1) at the 3rd step; and subjecting the purified extract fractionated with butanol (ATC1) to at least one further purification process selected from the group consisting of reverse phase partition chromatography, normal phase partition chromatography, ion exchange chromatography, and size exclusion chromatography to afford the purified extract with the secondary fractionation (ATC2) containing 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum* to treat and prevent inflammatory, allergic or asthmatic disease.

Specifically, the term "further purification process" is selected from (i) reverse phase partition chromatography, (ii) normal phase partition chromatography, (iii) ion exchange chromatography or (iv) size exclusion chromatography, preferably, reverse phase partition chromatography or any chromatography using by any resin as a stationary phase which can retain non-polar substance while eluting polar substance, for example, Sephadex resin such as Sephadex, Sephadex LH20, Sephadex G-25, Sephadex G-10, Sepharose, Superdex, methylacrylate resin, carboxymethyl cellulose, sulphopropyl cellulose, carboxymethyl Sephadex, sulphopropyl Sephadex, carboxymethyl Sepharose, sulphopropyl Sepharose and the like; reverse polymer resin using by Stylene-divinylbenzen co-polymer such as Polymer X, HP20, PRP-hl Polymer and the like or Methacrylate support resin etc; normal Silica gel such as BPC (Bonded phase chromatography) product, Silica product procured from YMC Co. Ltd, Silica product procured from DAISO Co. Ltd, Silica product procured from ASAHI Co. Ltd, Silica product procured from COSMOSYL Co. Ltd and the like; ODS product used for HPLC filler such as ODS product procured from YMC Co. Ltd, ODS product procured from DAISO Co. Ltd, ODS product procured from ASAHI Co. Ltd, ODS product procured from CHEMCO Co. Ltd, ODS product procured from Merck Co. Ltd ODS product procured from COSMOSYL Co. Ltd ODS product procured from FUJI Co. Ltd and the like.

In a preferred embodiment adopting (i) reverse phase partition chromatography as a further purification process of the present invention, the "stationary phase in the above-described reverse phase partition chromatography" may be any stationary phases such as reverse phase substance as a stationary phase which can retain non-polar substance while eluting polar substance, preferably, Silica gel based stationary phase, polymer based stationary phase such as polystyrene etc and the like, more preferably, Silica gel derivatives such as C2, C4, C6, C8, C10, C12, 14, C16, C18 and the like; or a polymer based stationary phase such as PS-2, Oasis HLB and the like, more and more preferably, reverse phase Silica gel (C18(IV)-D), ODS-A/ODS-AQ product from YMC Co. Ltd., SP-C-ODS product from CHEMCO Co. Ltd., SP-ODS-RPS product from DAISO Co. Ltd., 5C18 product from COSMOSYL Co. Ltd., Chromatorex product from FUJI Co. Ltd., etc.

In a preferred embodiment adopting (i) reverse phase partition chromatography as a further purification process of the present invention, the "mobile phase in the above-described (i) reverse phase partition chromatography" may be at least one solvent selected from water, acetonitrile, lower alcohol such as methanol, ethanol, butanol etc, tetrahydrofuran (THF) or the mixture thereof, preferably, water, lower alcohol such as methanol, ethanol, butanol etc, or the mixture thereof, more preferably, the mixture solvent of water and methanol, more and more preferably, the mixture solvent of water and methanol with starting from 90:10 (v/v) to 60:40 (v/v) to elute polar substance.

In a preferred embodiment adopting (ii) normal phase partition chromatography as a further purification process of the present invention, the "stationary phase in the above-described normal phase partition chromatography" may be any stationary phases such as normal phase substance as a stationary phase which can retain polar substance while eluting non-polar substance, preferably, Silica gel, Fluorosyl, or alumina based stationary phase, CN, Diol, or NH2 moiety polymer based stationary phase and the like, more preferably, Silica gel, Fluorosyl, or alumina based stationary phase, etc.

In a preferred embodiment adopting (ii) normal phase partition chromatography as a further purification process of the present invention, the "mobile phase in the above-described (ii) normal phase partition chromatography" may be at least one solvent selected from hexane, heptane, ethylacetate, ethanol, diethylether, 2-propanol or the mixture thereof, preferably, hexane, heptane, ethylacetate or the mixture thereof to elute non-polar substance.

In a preferred embodiment adopting (iii) ion exchange chromatography as a further purification process of the present invention, the "stationary phase in the above-described (iii) ion exchange chromatography" may be any high molecular stationary phases as a stationary phase which have charged cross-linking moiety, preferably, cation exchange resin, anion exchange resin, or synthetic adsorbent, and the like, more preferably, strongly acidic cation exchange resin such as AG 50W-x8, Amberlite IR-120, Dowex 60W-x8, SKIB etc; weakly acidic cation exchange resin such as Amberlite IRA-67, Dowex 3-x4A etc; strongly basic cation exchange resin such as DIAION SKIB, DIAION PK216, DIAION CR20, DIAION UBK555 (Mitsubishi Chemical Co.), TRILITE SPC 160H, TRILITE SPC 180H, TRILITE SPC 400JH (Samyang Co. Ltd.), AMBERLITE 200C Na, AMBERLITE CG50, AMBERLITE CR1310 Na, AMBERJET 200H, AMBERLYST 131 WET, ALBERLYST 232 WET (ROHM and HAAS Co. Ltd.), Lewatit VP OC 1800, Lewatit VP OC 1812, Lewatit MDS1368 Na, Lewaitit K1221 (Bayer Co. Ltd.), PUROLITE PCR833CA, PUROLITE C145 (Purolite Co. Ltd.), MFG210, MFG 250 (Finex Co. Ltd.) etc; strongly basic anion exchange resin such as SA11A, SA20A, SA21A etc; or CaptoQ (GE Healthcare Co. Ltd.), or the resin having similar property thereto such as Toyopearl QEA (Tosoh Co. Ltd.), Q Sepharose FF (GE Healthcare Co. Ltd.), Fractogel EMD, Fractogel TMAE, Fractogel HICAP (Merck KGaA Co. Ltd or Darmstadt Co. Ltd.); more and more preferably, SA21A; adsorbent such as SP207, HP20SS, HP20 etc, more preferably, HP 20.

In a preferred embodiment adopting (iv) size exclusion chromatography as a further purification process of the present invention, the "stationary phase in the above-described (iv) size exclusion chromatography" may be any gel type stationary phases as a stationary phase which can separate by the size of sample, preferably, dextran-based gel such as sephadex (for example, sephadex G-25), polyacrylamide-based gel such as Sephacryl (for example, Sephacryl-5400), Agarose-based gel such as Superose or Sepharose (for example, Sepharose CL-4B) or the combinations thereof such as Superdex 200 combination Dextran (For example, Sephadex™), or cross-linked Agarose gel (Superose™) and the like, however it shall be not limited thereto herein. The "mobile phase in the above-described (iv) size exclusion chromatography" may be buffer solution selected from the group consisting of sodium acetate buffer, sodium phosphate buffer, ammonium acetate buffer, MES (2-(N-morpholino)ethanesulphonic acid), Bis-Tris[2-Bis(2-hydroxyethyl)amino-2-(hydroxymethyl)-1,3-propandiol], ADA [N-(2-acetamido)iminodiacetate), PIPES [piperaxine-N,N'-Bis(2-ethanesulophonic acid)], BES [N.N'-Bis(2-hydroxyethyl)-2-aminoethansulphonic acid), MOPS [3-(N-morpholino)propansulphonic acid)], TES (N-Tris (hydroxymethyl)methyl-2-aminoethanesulphonic acid], HEPES [N-2-hydroxyethyl-piperazine-N'-2-ethanesulphonic acid), and the like; preferably, sodium acetate buffer, sodium phosphate buffer, or ammonium acetate buffer.

In a preferred embodiment of the present invention, the present invention can also perform (v) Gel permeation chromatography or Gel filtration chromatography in addition to (i) reverse phase partition chromatography, (ii) normal phase partition chromatography, (iii) ion exchange chromatography, (iv) size exclusion chromatography or the combination thereof, as a further purification process disclosed herein.

The present invention also provides novel purified extract such as (a) the purified extract fractionated with butanol (designated as "ATC1" hereinafter) or (b) the purified extract with the secondary fractionation (designated as "ATC2" hereinafter) prepared by the above-described preparation methods.

The present invention also provides novel purified extract fractionated with butanol (ATC1) from the extract of *Pseudolysimachion rotundum* var *subintegrum*, prepared by the above-described preparation methods, which contains 12.3-47% (w/w) catalposide derivatives in total extract (100%) of *Pseudolysimachion rotundum* var *subintegrum* wherein said catalposide derivatives consist of 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol, preferably, 20-25% (w/w) verproside, 0.5-5% (w/w) veratric acid, 1-5% (w/w) catalposide, 0.5-5% (w/w) picroside II, 0.5-5% (w/w) isovanilloyl catalpol and 1-5% (w/w) 6-O-veratroyl catalpol based on the weight of total extract (100%) of *Pseudolysimachion rotundum* var *subintegrum*.

The present invention also provides novel purified extract fractionated with butanol (ATC1) from the extract of *Pseudolysimachion rotundum* var *subintegrum*, prepared by the above-described preparation methods, which shows the relative mixed ratio (w/w) between the weight of each catalposide derivative of 15.0-18.0 (w/w) verproside, 2.10-2.60 (w/w) catalposide, 1 (w/w) picroside II, 1.00-1.30 (w/w) isovanilloyl catalpol and 2.00-2.30 (w/w) 6-O-veratroyl catalpol; preferably, 16.0-17.0 (w/w) verproside, 2.20-2.50 (w/w) catalposide, 1 (w/w) picroside II, 1.10-1.20 (w/w) isovanilloyl catalpol and 2.10-2.20 (w/w) 6-O-veratroyl catalpol; more preferably, 16.20-16.99 (w/w) verproside, 2.40-2.45 (w/w) catalposide, 1 (w/w) picroside II, 1.10-1.19 (w/w) isovanilloyl catalpol and 2.10-2.19 (w/w) 6-O-veratroyl catalpol.

The present invention also provides novel purified extract with the secondary fractionation (ATC2) from the extract of *Pseudolysimachion rotundum* var *subintegrum*, prepared by the above-described preparation methods, which contains 36.5-91% (w/w) catalposide derivatives in total extract (100%) of *Pseudolysimachion rotundum* var *subintegrum*, wherein said catalposide derivatives consist of 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum*; preferably, 40-50% (w/w) verproside, 1-5% (w/w) veratric acid, 3-10% (w/w) catalposide, 2-5% (w/w) picroside II, 2-8% (w/w) isovanilloyl catalpol and 3-8% (w/w) 6-O-veratroyl catalpol based on the weight of total extract (100%) of *Pseudolysimachion rotundum* var *subintegrum*.

The present invention also provides novel purified extract with the secondary fractionation (ATC2) from the extract of *Pseudolysimachion rotundum* var *subintegrum*, prepared by the above-described preparation methods, which show the relative mixed ratio (w/w) between the weight of each catalposide derivative, of 13.0-16.0 (w/w) verproside, 2.20-2.50 (w/w) catalposide, 1 (w/w) picroside II, 1.10-1.40 (w/w) isovanilloyl catalpol and 2.00-2.20 (w/w) 6-O-veratroyl catalpol; preferably, 14.0-15.0 (w/w) verproside, 2.30-2.45 (w/w) catalposide, 1 (w/w) picroside II, 1.20-1.35 (w/w) isovanilloyl catalpol and 2.00-2.10 (w/w) 6-O-veratroyl catalpol; more preferably, 14.50-14.99 (w/w) verproside, 2.35-2.43 (w/w) catalposide, 1 (w/w) picroside II, 1.15-1.24 (w/w) isovanilloyl catalpol and 2.01-2.09 (w/w) 6-O-veratroyl catalpol.

The term "purified extract" disclosed herein may be used as a dried form prepared by the vacuum evaporation method, freeze dry method or hot-air drying method etc.

The term "inflammatory disease" disclosed herein comprises eczema, atopic dermatitis, conjunctivitis, periodontal disease, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, systemic lupus erythematosus, fibromyalgia, psoriatic arthritis, osteoarthritis, rheumatic arthritis, periarthritis of shoulder, tendinitis, tenosynovitis, peritendinitis, myositis, hepatitis, cystitis, nephritis, Sjogren's syndrome, multiple sclerosis, chronic inflammatory disease, acute inflammatory disease etc, but not intended herein to limit thereto, preferably, eczema, atopic dermatitis, rheumatic arthritis, chronic inflammatory disease, acute inflammatory disease etc, The term "allergic disease" disclosed herein comprises allergic rhinitis, allergic dermatitis, contact dermatitis, hives, insect allergy, food allergy, drug allergy, allergic conjunctivitis, hypersensitivity etc, but not intended herein to limit thereto, preferably, allergic rhinitis, allergic dermatitis, contact dermatitis, hives, insect allergy, food allergy, drug allergy, more preferably, allergic dermatitis, contact dermatitis.

The term "asthmatic disease" disclosed herein comprises any asthma caused by various external factors, but not intended herein to limit thereto, such as dust mites, animal's fur or dandruff, cockroaches, food, drug, cough, cigarette smoke, air pollution, food additive, physical activity such as exercise etc, weather change, yellow sand, stress etc.

The term "prevent" disclosed herein comprises any act to inhibit or postpone the occurrence of certain disease or disorder disclosed herein by way of administrating the inventive composition; and the term "treat" disclosed herein comprises any act to alleviate or favorably changing the symptom associated with certain disease or disorder disclosed herein by way of administrating the inventive composition.

The present inventors have found that the novel industrialized method for preparing purified extract can provide more abundant active ingredients, i.e., 36.5% to 91.0% (w/w) such as catalpol derivatives from the extract of *Pseudolysimachion rotundum* var *subintegrum* comparing with the crude extract prepared by the conventional method disclosed in the prior art wherein the content of catalpol derivatives in only 8.49% (w/w) through various HPLC analyses, for example, the inventive purified extract (ATC1) contains 17.60% (w/w) verproside, 0.72% (w/w) veratric acid, 2.62% (w/w) catalposide, 1.08% (w/w) picroside II, 1.26% (w/w) isovanilloyl catalpol and 2.36% (w/w) 6-O-veratroyl catalpol (See Example 2) and the inventive purified extract (ATC2) contains 43.83% (w/w) verproside, 1.80% (w/w) veratric acid, 7.07% (w/w) catalposide, 2.93% (w/w) picroside II, 3.85% (w/w) isovanilloyl catalpol and 6.15% (w/w) 6-O-veratroyl catalpol while the crude extract (CX) prepared by the conventional method disclosed in the prior art contains only 5.9% (w/w) verproside, 0.21% (w/w) veratric acid, 0.82% (w/w) catalposide, 0.40% (w/w) picroside II, 0.42% (w/w) isovanilloyl catalpol and 0.74% (w/w) 6-O-veratroyl catalpol based on the weight of total extract (100%) of *Pseudolysimachion rotundum* var *subintegrum*; crude extract; as well as the inventive purified extract showed more potent anti-inflammatory, anti-allergy and anti-asthma activity than that prepared by the conventional preparation method through various in vivo test such as inhibition test on the reproduction of eosinolphil, the release of immunoglobulin and inflammatory chemokines in plasma and bronchoalveolar fluid as well as the suppression of airway hyperresponsiveness and golblet cell hyperplasia in a OVA-sensitized/challenged mouse model.

Accordingly, in accordance with the other aspect of the present invention, present invention provide a pharmaceutical composition comprising the purified extract containing abundant active ingredients prepared by the above-described methods from *Pseudolysimachion rotundum* var *subintegrum* as an active ingredient for the treatment and prevention of inflammatory, allergic or asthmatic disease.

Present invention provide a pharmaceutical composition comprising the purified extract containing abundant active ingredients prepared by the above-described methods from *Pseudolysimachion rotundum* var *subintegrum* as an active ingredient and the pharmaceutically acceptable carriers or excipients, for the treatment and prevention of inflammatory, allergic or asthmatic disease.

In accordance with another aspect of the present invention, there is also provided a use of the purified extract containing abundant active ingredients prepared by the above-described methods from *Pseudolysimachion rotundum* var *subintegrum* for manufacture of medicines employed for treating or preventing inflammatory, allergic or asthmatic disease.

The term "pharmaceutically acceptable carriers or excipients" defined herein comprises "pharmaceutical additives, the inactive ingredients used to make up a medication. They include dyes, flavors, binders, emollients, fillers, lubricants, preservatives, and many more classifications. Common excipients include cornstarch, lactose, talc, magnesium stearate, sucrose, gelatin, calcium stearate, silicon dioxide, shellac and glaze, which has been well-known in the art (See, Home-page of Food and Drug Administration: or drug information online) or previous literature (for example, Rowe, Raymond C et al., Handbook of Pharmaceutical Excipients, Pharmaceutical Press, 7th Edition, 2012).

In accordance with another aspect of the present invention, there is also provided a method of treating or preventing inflammatory, allergic or asthmatic disease in mammals, wherein the method comprises administering a therapeutically effective amount of the purified extract containing abundant active ingredients prepared by the above-described methods from *Pseudolysimachion rotundum* var *subintegrum* into the mammal suffering from inflammatory, allergic or asthmatic diseases.

The inventive composition for treating and preventing inflammatory, allergic or asthmatic disease may comprises above extracts as 0.1-99%, preferably, 0.1-50% by weight based on the total weight of the composition.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract varies depending on the condition and the weight of the subject, severity, drug form, route and period of administration, and may be chosen by those skilled in the art. However, in order to obtain desirable effects, it is generally recommended to administer at the amount ranging from 0.0001 to 1000 mg/kg, preferably, 0.001 to 100 mg/kg by weight/day of the inventive extract of the present invention. The dose may be administered in single or divided into several times per day. The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

The inventive extract of the present invention also can be used as a main component or additive and aiding agent in the preparation of various functional health food and health care food.

Accordingly, it is the other object of the present invention to provide a health functional food comprising the purified extract containing abundant active ingredients prepared by the above-described methods from *Pseudolysimachion rotundum* var *subintegrum* for the prevention or alleviation of inflammatory, allergic or asthmatic disease.

The term "a functional health food" defined herein" the functional food having enhanced functionality such as physical functionality or physiological functionality by adding the extract of the present invention to conventional food to prevent or improve the purposed diseases in human or mammal.

It is the other object of the present invention to provide a health care food comprising the purified extract containing abundant active ingredients prepared by the above-described methods from *Pseudolysimachion rotundum* var *subintegrum*, together with a sitologically acceptable additive for the prevention or alleviation of inflammatory, allergic or asthmatic disease.

The term "a health care food" defined herein "the food containing the extract of the present invention showing no specific intended effect but general intended effect in a small amount of quantity as a form of additive or in a whole amount of quantity as a form of powder, granule, capsule, pill, tablet etc.

The term "a sitologically acceptable additive" defined herein comprises "any substance the intended use which results or may reasonably be expected to result-directly or indirectly—in its becoming a component or otherwise affecting the characteristics of any food", and can be classified into three groups according to its origin, i.e., (1) chemically synthetic additive such as ketones, glycine, potassium citrate, nicotinic acid, etc; (2) natural additive such as persimmon dye, licorice extract, crystalline cellulose, guar gum etc; (3) the mixed additive therewith such as sodium L-glutamate, preservatives, tar dye etc, or various categories according to its function in the food, for example, thickening agent, maturing agent, bleaching agent, sequestrant, humectant, anti-caking agent, clarifying agents, curing agent, emulsifier, stabilizer, thickener, bases and acid, foaming agents, nutrients, coloring agent, flavoring agent, sweetener, preservative agent, anti-oxidant, etc, which has been well-known in the art or previous literature (See, "Codex General Standard for Food Additives" (GSFA, Codex STAN 192-1995) in Home-page of GSFA Online).

If a substance is added to a food for a specific purpose in that food, it is referred to as a direct additive and indirect food additives are those that become part of the food in trace amounts due to its packaging, storage or other handling.

The term "health care foods or health functional foods" disclosed herein can be contained in food, health beverage, dietary supplement etc, and may be formulated into a form of pharmaceutically dosing form such as a powder, granule, tablet, suspension, emulsion, syrup, chewing tablet, capsule, beverage etc; or the food form, for example, bread, rice cake, dry fruit, candy, chocolate, chewing gum, ice cream, milk such as low-fat milk, lactose-hydrolyzed milk, goat-milk, processed milk, milk product such as fermented milk, butter, concentrated milk, milk cream, butter oil, natural cheese, processed cheese, dry milk, milk serum etc, processed meat product such as hamburger, ham, sausage, bacon etc, processed egg product, fish meat product such as fish cake etc, noodle products such as instant noodles, dried noodles, wet noodles, fried noodles, non-fried noodles, gelatinized dry noodles, cooked noodles, frozen noodles, Pasta etc, tea product such as tea bag, leached tea etc, health drinks such as fruit drinks, vegetable drinks, carbonated soft drinks, soymilk drinks, lactic beverage mixed beverage, etc, seasoning food such as soy sauce, soybean paste, red pepper paste, chunjang (a kind of fermented soybean product colored by caramel), cheonggukjang (natural fermented soybean by *B. subtillis*), mixed paste, vinegar, sauce, ketchup, curry, dressing etc, margarine, shortening, pizza etc, but not intended herein to limit thereto, for preventing or improving of purposed disease.

Also, above described extract can be added to food or beverage for prevention and improvement of purposed disorder. The amount of above described extract in food or beverage as a functional health food or health care food may generally range from about 0.01 to 100 w/w % of total weight of food for functional health food composition. In particular, although the preferable amount of the extract of the present invention in the functional health food, health care food or special nutrient food may be varied in accordance to the intended purpose of each food, it is preferably used in general to use as an additive in the amount of the extract of the present invention ranging from about 0.01 to 5% in food such as noodles and the like, from 40 to 100% in health care food on the ratio of 100% of the food composition.

Providing that the health beverage composition of present invention contains above described extract or compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, *stevia* extract such as levaudioside A, glycyrrhizin et al., and synthetic deodorant such as saccharin, aspartame et al., may be useful favorably. The amount of above described natural carbohydrate is generally ranges from about 1 to 20 g, preferably 5 to 12 g in the ratio of 100 Ml of present beverage composition.

The other components than aforementioned composition are various nutrients, a vitamin, a mineral or an electrolyte, synthetic flavoring agent, a coloring agent and improving agent in case of cheese, chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract or compound therein are various food, beverage, gum, vitamin complex, health improving food and the like.

Inventive extract of the present invention has no toxicity and adverse effect therefore; they can be used with safe.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

Advantageous Effects

As described in the present invention, inventive novel industrialized method for preparing purified extract containing more abundant active ingredients such as catalpol derivatives from the extract of *Pseudolysimachion rotundum* var *subintegrum* and the purified extract showed more potent anti-inflammatory, anti-allergy and anti-asthma activity than that prepared by the conventional preparation method disclosed in the prior art through various in vivo tests such as inhibition test on the reproduction of eosinolphil, the release of immunoglobulin and inflammatory chemokines in plasma and bronchoalveolar fluid as well as the suppression of airway hyperresponsiveness and golblet cell hyperplasia in a OVA-sensitized/challenged mouse model. Therefore, it can be used as the therapeutics or functional health food for treating and preventing inflammatory, allergic or asthmatic disease.

DESCRIPTION OF DRAWINGS

The above and other objects, features and other advantages of the present invention will more clearly understood from the following detailed description taken in conjunction with the accompanying drawings, in which.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Comparative Example 1

Preparation of the Crude Extract of *Pseudolysimachion rotundum* Var *Subintegrum*

1-1. Preparation of Crude Extract (ATE)

1 kg of dried *Pseudolysimachion rotundum* var *subintegrum* (cultivated at 244, Soi-myeon Eumseong-gun Chungcheongbuk-do in Korea according to GAP) cut into small pieces and mixed with 10 L of 40% ethanol. The mixture was stirred at room temperature for 24 hours and extracted with reflux extraction at 78° C. for 12 hours to collect the filtrate, three times. The extract was filtered with filter paper to remove the debris. The collected filtrate was concentrated by rotary evaporator (EYELA, N-2100, Japan) at 55-65° C. under reduced pressure and dried with freezing dryer to obtain 202 g of dried crude extract (designated as 'ACE" hereinafter) for used as a comparative example.

1-2. Preparation of Crude Extract (ATM)

1.1 kg of dried *Pseudolysimachion rotundum* var *subintegrum* (cultivated at 244, Soi-myeon Eumseong-gun Chungcheongbuk-do in Korea according to GAP) cut into small pieces and mixed with 5 L of methanol. The mixture was stirred at room temperature for 24 hours and extracted with reflux extraction at 78° C. for 12 hours to collect the filtrate, three times. The extract was filtered with filter paper to remove the debris. The collected filtrate was concentrated by rotary evaporator (EYELA, N-2100, Japan) at 55-65° C. under reduced pressure and dried with freezing dryer to obtain 100.5 g of dried crude extract (designated as 'ACM" hereinafter) for used as a comparative example.

1-3. Component Analysis

Figure 1:
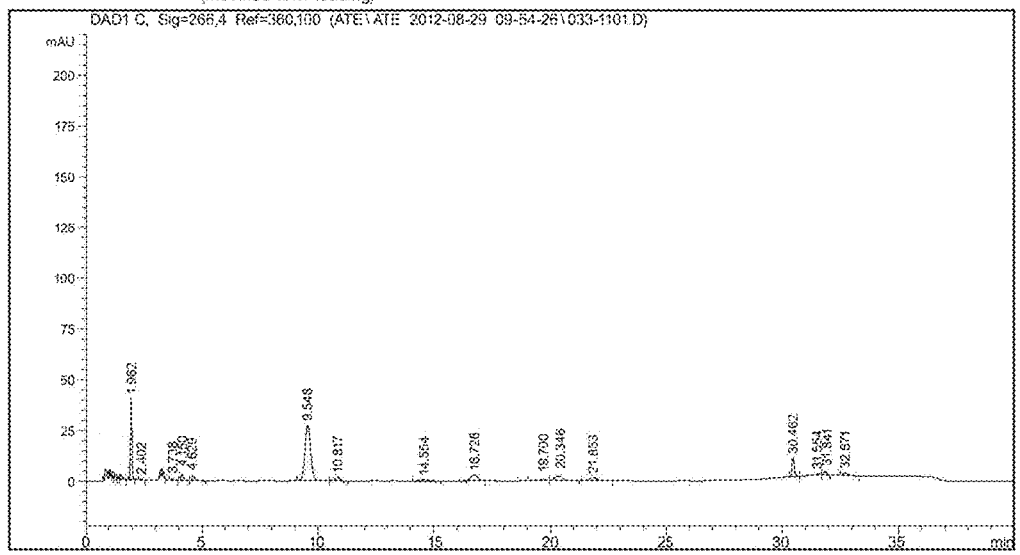
FIG. 1 shows HPLC analysis of the crude extract of *Pseudolysimachion rotundum* var *subintegrum* prepared in comparative Example 1.

The component analysis was performed using by HPLC (Agilent 1260 model, USA) according to the condition in Table 1 and the result was shown in FIG. 1.

As can be seem in FIG. 1, it has been confirmed that each ingredient was detected at 9.548 mins (Verproside), 10.817 mins (Veratric acid), 16.728 mins (Catalposide), 20.346 min (Picroside II), 21.853 mins (Isovanilloyl catalpol), and 30.462 mins (6-O-veratrolyl catalpol) respectively.

The content of each ingredient (%) in the sample was calculated based on the HPLC pattern (retention time) according to math formulae 1.

$$\text{content of each ingredient} = \text{conc. of standard (mg/ml)} / \text{conc. of test sample (mg/ml)} \times At/As \times \text{purity of standard (\%)} \qquad \text{Math formulae 1}$$

wherein "At" denotes the ingredient area in test sample and "As" denotes that in standard provided that the sampled volume of test sample and standard is identical to each other.

TABLE 1

| HPLC condition | |
|---|---|
| HPLC condition | |
| Pump | Agilent 1260 Series, 1260 quart pump |
| Detector | Agilent 1260 Series, 1260 DAD |
| Column | Agilent Eclipse XOB C18, 4.6 × 50 cm, 5 μm |
| Flow rate | 1.5 ml/min |
| UV Absorbance | 266 nm |
| Mobile phase | Mobile phase A: phosphate buffer (pH = 3.5) |
| | Mobile phase B: methanol |

| Time | Mobile phase A (%) | Mobile phase B (%) |
|---|---|---|
| 0~5 | 80 | 20 |
| 5~20 | 75 | 25 |
| 20~25 | 75 | 25 |

TABLE 1-continued

| HPLC condition | | |
|---|---|---|
| HPLC condition | | |
| 25~30 | 55 | 45 |
| 30~35 | 55 | 45 |
| 35~36 | 80 | 20 |
| 36~40 | 80 | 20 |
| Injection volume | 10 μl | |

At the result, it has been confirmed that the crude extract of *Pseudolysimachion rotundum* var *subintegrum* contains only 8.49% (w/w) catalposide derivatives, i.e., 5.9% (w/w) verproside, 0.21% (w/w) veratric acid, 0.82% (w/w) catalposide, 0.40% (w/w) picroside II, 0.42% (w/w) isovanillyl catalpol, and 0.74% (w/w) 6-O-veratroyl catalpol, respectively, as can be seen in Table 2.

TABLE 2

HPLC result (crude extract: ACE)

| | Comparative Example 1 | |
|---|---|---|
| Active ingredient | Retention Time (mins) | Content (w/w %) |
| Verproside | 9.548 | 5.90 |
| Veratric acid | 10.817 | 0.21 |
| Catalposide | 16.728 | 0.82 |
| Picroside II | 20.346 | 0.40 |
| Insovanilloyl catalpol | 21.853 | 0.42 |
| 6-O-veratroyl catalpol | 30.462 | 0.74 |
| Total | | 8.49 |

Example 1. Preparation of the Purified Extract (ATC1) of *Pseudolysimachion rotundum* Var Subintegrum The crude extract (ACE) of *Pseudolysimachion rotundum* var *subintegrum* prepared by the conventional method according to Comparative Example 1, was suspended in 2 L of distilled water and the suspension was added with 2 L of butanol to fractionate into butanol-soluble fraction and water-soluble fraction. The butanol soluble fraction was collected, concentrated under reduced pressure and dried to afford 82 g of the inventive purified extract fractionated with butanol (ATC1) used as a test example.

Figure 2:
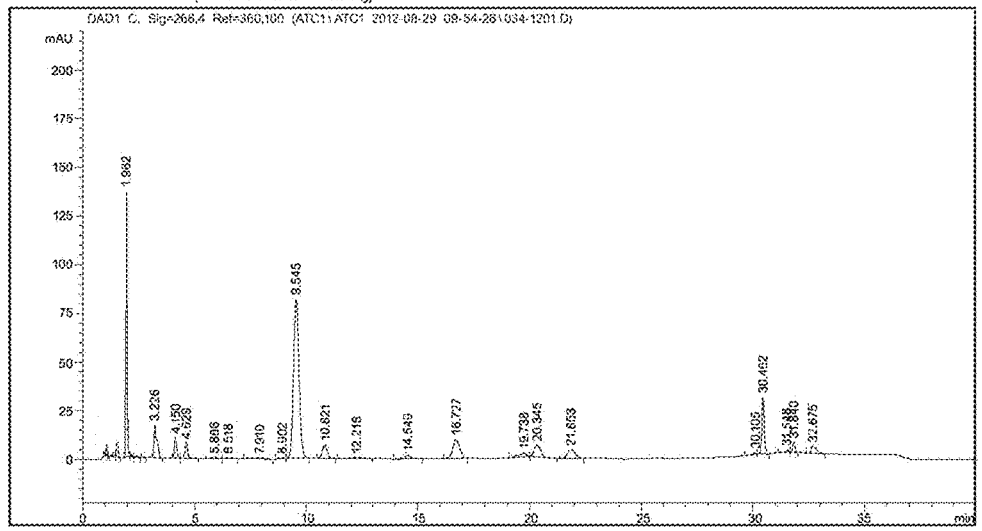
FIG. 2 shows HPLC analysis of the inventive purified extract (ATC1) of *Pseudolysimachion rotundum* var *subintegrum* prepared in Example 1.

The component analysis was performed using by HPLC (Agilent 1260 model, USA) according to the condition in Table 1 and the result was shown in FIG. 2.

As can be seem in FIG. 2, it has been confirmed that each ingredient was detected at 9.545 mins (Verproside), 10.821 mins (Veratric acid), 16.727 mins (Catalposide), 20.345 min (Picroside II), 21.853 mins (Isovanilloyl catalpol), and 30.462 mins (6-O-veratroyl catalpol) respectively.

The content of each ingredient (%) in the sample was calculated based on the HPLC pattern (retention time) according to math formulae 1.

At the result, it has been confirmed that the inventive purified extract fractionated with butanol (ATC1) of *Pseudolysimachion rotundum* var *subintegrum* contains 25.64% (w/w) catalposide derivatives, i.e., 17.60% (w/w) verproside, 0.72% (w/w) veratric acid, 2.62% (w/w) catalposide, 1.08% (w/w) picroside II, 1.26% (w/w) isovanillyl catalpol, and 2.36% (w/w) 6-O-veratroyl catalpol, respectively, as can be seen in Table 3.

TABLE 3

HPLC result (purified extract: ATC1)

| | Example 1 | |
|---|---|---|
| Active ingredient | Retention Time (mins) | Content (w/w %) |
| Verproside | 9.545 | 17.60 |
| Veratric acid | 10.821 | 0.72 |
| Catalposide | 16.727 | 2.62 |
| Picroside II | 20.345 | 1.08 |
| Insovanilloyl catalpol | 21.853 | 1.26 |
| 6-O-veratroyl catalpol | 30.462 | 2.36 |
| Total | | 25.64 |

Example 2. Preparation of the Purified Extract (ATC2) of *Pseudolysimachion rotundum* Var Subintegrum The inventive purified extract fractionated with butanol (ATC1) of *Pseudolysimachion rotundum* var *subintegrum* according to Example 1, was dissolved in 75 mL of mixed solvent (distilled water:methanol=1:0.003) and 75 g of the solution was loaded on reverse phase column chromatography (C18(IV)-D-75-120 nm, AGC Si-Tech Co. Ltd., Japan, 450 g) with eluting the suspension using by eluting solvent (distilled water:methanol=90:10→60:40). 8.4 L of the eluted solution running at the initial eluting solvent system (distilled water:methanol=90:10) was collected and concentrated under reduced pressure. 5.6 L of the eluted solution running at the late eluting solvent system (distilled water: methanol=60:40) was collected, concentrated under reduced pressure and dried to afford 33 g of the inventive purified extract with the secondary fractionation (ATC2) used as a test example.

Figure 3:
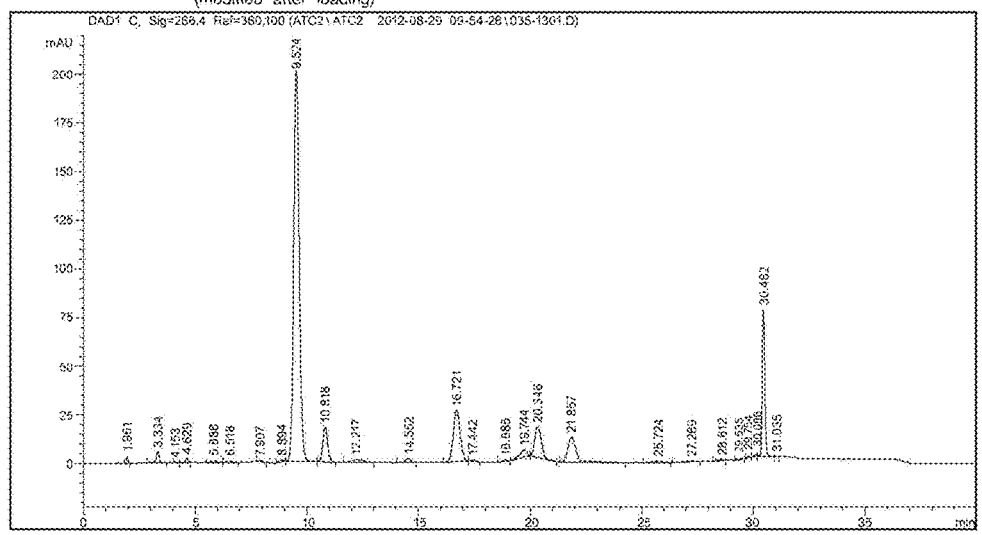
FIG. 3 shows HPLC analysis of the inventive purified extract (ATC2) of *Pseudolysimachion rotundum* var *subintegrum* prepared in Example 2.

The component analysis was performed using by HPLC (Agilent 1260 model, USA) according to the condition in Table 1 and the result was shown in FIG. 3.

As can be seem in FIG. 3, it has been confirmed that each ingredient was detected at 9.525 mins (Verproside), 10.818 mins (Veratric acid), 16.721 mins (Catalposide), 20.346 min (Picroside II), 21.857 mins (Isovanilloyl catalpol), and 30.462 mins (6-O-veratroyl catalpol) respectively.

The content of each ingredient (%) in the sample was calculated based on the HPLC pattern (retention time) according to math formulae 1.

At the result, it has been confirmed that the inventive purified extract with the secondary fractionation (ATC2) of *Pseudolysimachion rotundum* var *subintegrum* contains 65.63% (w/w) catalposide derivatives, i.e., 43.83% (w/w) verproside, 1.80% (w/w) veratric acid, 7.07% (w/w) catalposide, 2.93% (w/w) picroside II, 3.85% (w/w) isovanillyl catalpol, and 6.15% (w/w) 6-O-veratroyl catalpol, respectively, as can be seen in Table 4.

TABLE 4

HPLC result (purified extract: ATC2)

| | Example 2 | |
|---|---|---|
| Active ingredient | Retention Time (mins) | Content (w/w %) |
| Verproside | 9.524 | 43.83 |
| Veratric acid | 10.818 | 1.80 |
| Catalposide | 16.721 | 7.07 |
| Picroside II | 20.346 | 2.93 |

TABLE 4-continued

HPLC result (purified extract: ATC2)

Example 2

| Active ingredient | Retention Time (mins) | Content (w/w %) |
|---|---|---|
| Insovanilloyl catalpol | 21.857 | 3.85 |
| 6-O-veratroyl catalpol | 30.462 | 6.15 |
| Total | | 65.63 |

TABLE 5

The level of total IgE in blood serum

| | | total IgE (mg/ml) |
|---|---|---|
| NC | | 0.57 ± 0.02 |
| OVA | | 5.23 ± 0.34 |
| ATC1 | 30 mg/kg | 2.05 ± 0.12 |
| | 100 mg/kg | 2.14 ± 0.25 |
| ATM | 30 mg/kg | 3.09 ± 0.54 |
| | 100 mg/kg | 2.49 ± 0.35 |
| Monte30 | | 1.82 ± 0.40 |

Experimental Example 1. Preliminary Determination of the Total Serum IgE Level in OVA-Sensitized/Challenged Mouse Model In order to found the purified extract showing more pharmacologically potent activity than the crude extract prepared in comparative Example, following preliminary test was performed by the method disclosed in the literature (Elias, J. A. et al., *J. Clin. Invest.*, 111, pp 297-297, 2003).

1-1. Animal Sensitization and Airway Challenge

Specific pathogen-free female BALB/c mice (about 20 g), aged 6 weeks, which were routinely screened serologically for relevant respiratory pathogens, were purchased from ORIENT Co. (Seoul, Korea) and acclimated with the experimental environment for 1 week.

Briefly, mice were sensitized by intraperitoneal injection of 20 μg OVA (Ovalbumin; A5503, Sigma, St. Louis, Mo.), which was emulsified in 2 mg aluminum hydroxide in 200 μl of PBS buffer (pH 7.4), biweekly. The mice were challenged through the airways with OVA (1% in PBS) for 30 min using an ultrasonic nebulizer (NE-U12; Omron Corp., Tokyo, Japan) from the 28th day to 34th day after the initial sensitization. 24 hrs after the antigen treatment, the airway hyperresponsiveness was determined and the mice were sacrificed 48 hrs after the last challenge. The mice were sacrificed with an overdose of pentobarbital (Entobal®, Hanrim Pharm. Co. Ltd.) 24 h after the last challenge, and a tracheotomy was performed. After 1.2 ml of physiological saline solution (PBS) was instilled into the lungs, bronchoalveolar lavage fluid (BALF) was obtained by aspiration three times (total 1.5 ml) via tracheal cannulation.

The groups were divided into several groups, i.e., (a) normal control group (NC): the groups treated or not-treated with OVA; (b) asthma-induced group (OVA): the groups treated with OVA to induce asthma; and (c) comparative group: the groups treated with positive control group (M30, montelukast; 30 mg/kg, PO, Sigma-Aldrich Co. Ltd., SML 0101) 1 hr prior to OVA inhalation.

The test group consists of 6 mice for each group and 1 hour prior to OVA inhalation, various concentrations of the test sample, ATC1 (30 mg/kg and 100 mg/kg) and ATM (30 and 100 mg/kg) were orally administrated to the mice.

As shown in Table 5, the total level of IgE in blood serum in asthma-induced group (OVA) was significantly increased whereas those in the test sample group orally administrated with various concentrations of test samples (ATC1, 30 mg/kg and 100 mg/kg) were more reduced than that in the group treated with crude extract of *Pseudolysimachion rotundum* var *subintegrum* (ATM, 30 and 100 mg/kg). (See Table 5)

Experimental Example 2. Anti-Asthamtic Effect Using by Airway Hyperresponsiveness Test in a OVA-Sensitized/Challenged Mouse Model In order to confirm the anti-asthmatic effect of test samples prepared in Examples using by airway hyperresponsiveness test in a OVA-sensitized/challenged mouse model, following test was performed by the method disclosed in the literature (Elias, J. A. et al., *J. Clin. Invest.*, 111, pp 297-297, 2003).

1-1. Animal Sensitization and Airway Challenge

Specific pathogen-free female BALB/c mice (about 20 g), aged 6 weeks, which were routinely screened serologically for relevant respiratory pathogens, were purchased from ORIENT Co. (Seoul, Korea) and acclimated with the experimental environment for 1 week.

Briefly, mice were sensitized by intraperitoneal injection of 20 μg OVA (Ovalbumin; A5503, Sigma, St. Louis, Mo.), which was emulsified in 2 mg aluminum hydroxide in 200 μl of PBS buffer (pH 7.4), biweekly. The mice were challenged through the airways with OVA (1% in PBS) for 30 min using an ultrasonic nebulizer (NE-U12; Omron Corp., Tokyo, Japan) from the 28th day to 34th day after the initial sensitization. 24 hrs after the antigen treatment, the airway hyperresponsiveness was determined and the mice were sacrificed 48 hrs after the last challenge. The mice were sacrificed with an overdose of pentobarbital (Entobal®, Hanrim Pharm. Co. Ltd.) 24 h after the last challenge, and a tracheotomy was performed. After 1.2 ml of physiological saline solution (PBS) was instilled into the lungs, bronchoalveolar lavage fluid (BALF) was obtained by aspiration three times (total 1.5 ml) via tracheal cannulation.

Group of mice (n=6) were studied; they received the following treatment: (1) The non-treatment group with OVA as a normal control group (NC); (2) The control group treated and inhaled with OVA as an asthma induced group (OVA); (3) The positive control group treated with known asthma therapeutics (Montelukast; 30 mg/kg, PO, Sigma-Aldrich Korea, SML-0101, M30) 1 hour prior to OVA inhalation; (4) The test sample group orally administered with various concentrations of test samples, i.e., 5 mg/kg, 10 mg/kg, 25 mg/kg and 50 mg/kg of purified extract (ATC2) 1 hour prior to OVA inhalation.

1-2. Evaluation of Airway Hyperresponsiveness

In order to evaluate the airway hyperresponsiveness of the mice, the airway resistance was determined using by apparatus (One chamber whole body plethymography, OCP3000, All Medicus, Seoul. Korea) and the determined value was statistically calculated by Pehn value (Enhance Pause) reflecting on the degree of airway obstruction. The Penh value was determined for 3 mins by the process of determining the basal value at the eupnea phase and determining the Penh value after inhaling PBS with Ultrasonic nebulizer (NE-U12, IMRON Corp., Tokyo, JAPAN) for 3 mins.

Figure 4:
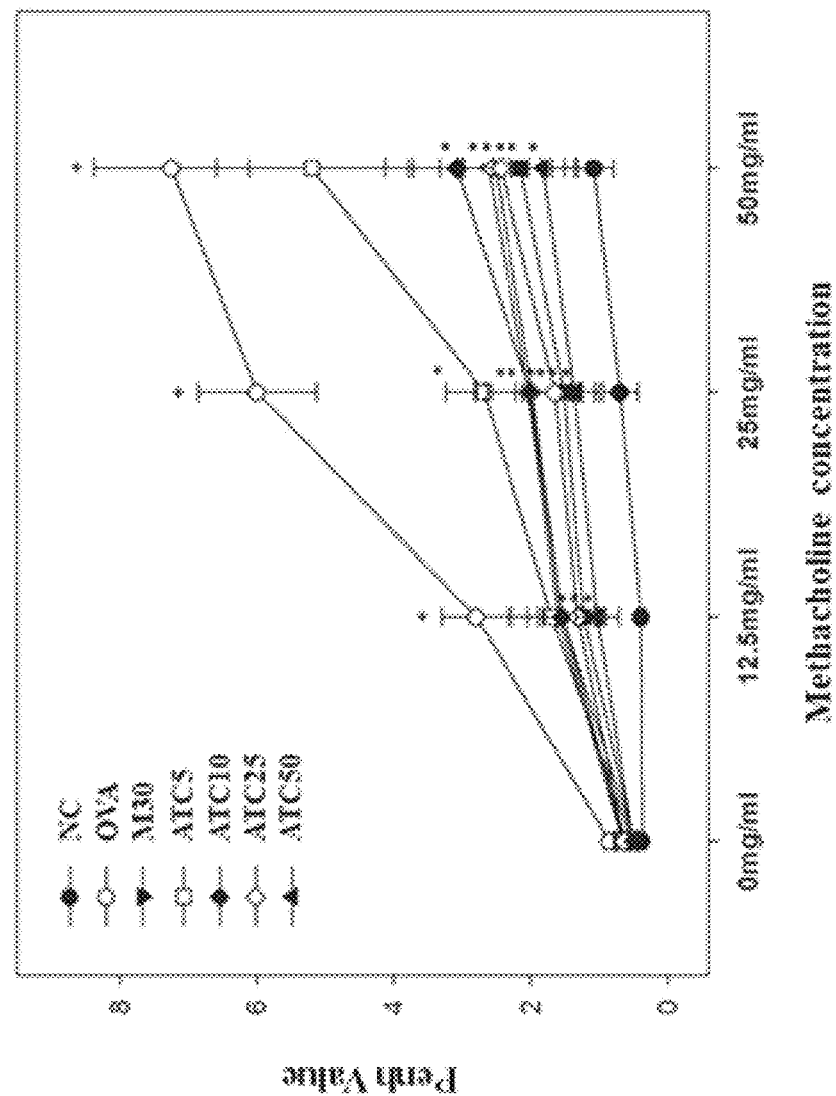
FIG. 4 shows the suppressive effect of the inventive purified extract on airway hyperresponsiveness in a OVA-sensitized/challenged mouse model.

Thereafter, various concentrations of methacholine (A2251, Sigma, St. Louis, Mo.), 12, 25 and 50 mg/ml, were inhaled with increasing concentration to determine the Pehn values. The increase of Penh value was expressed as percentage (%) after the methacholine inhalation and the Penh value of basal line was set to 100%. The value of Pehn was calculated according to math formulae 2 and the result was shown in FIG. 4.

$$Pehn = (Te/RT - 1) \times PEF/PIF \quad \text{Math formulae 2}$$

Te: Expiration Time (The period from a inhalation to the next inhalation);
RT: Relaxation Time (The period that the exhaled volume is reached to the extent to 30% of one expiration volume during expiration)
PEF: Peak Expiration Flow
PIF: Peak Inspiration Flow At the result, it has been confirmed that the Penh value in the control group treated and inhaled with OVA as an asthma induced group (OVA) was sharply increased while that in the non-treatment group with OVA as a normal control group (NC) had been gradually increased with increasing the concentration of methancholine.

In a while, the Penh value in the positive control group treated with Montelukast (MO) as well as the test sample group orally administrated with various concentrations of test samples (ATC-10, ATC-25, and ATC-50) were significantly reduced regardless of the concentration of methacholine. (See Table 6)

TABLE 6

| | | Penh Value | | | |
|---|---|---|---|---|---|
| | | Methacholine (Conc. mg/Ml) | | | |
| | | 0 | 12.5 | 25 | 50 |
| NC | | 0.37 ± 0.03 | 0.39 ± 0.04 | 0.69 ± 0.14 | 1.07 ± 0.18 |
| OVA | | 0.85 ± 0.10 | 2.79 ± 0.25 | 5.99 ± 0.92 | 7.24 ± 0.74 |
| ATC2 | 5 | 0.52 ± 0.05 | 1.69 ± 0.27 | 2.68 ± 0.52 | 5.19 ± 0.74 |
| (mg/kg) | 10 | 0.63 ± 0.06 | 1.54 ± 0.18 | 2.01 ± 0.52 | 3.08 ± 0.40 |
| | 25 | 0.64 ± 0.08 | 1.31 ± 0.17 | 1.64 ± 0.31 | 2.43 ± 0.33 |
| | 50 | 0.51 ± 0.06 | 1.02 ± 0.17 | 1.36 ± 0.09/ | 1.82 ± 0.28 |
| M30 | | 0.49 ± 0.04 | 1.54 ± 0.20 | 1.98 ± 0.37 | 2.51 ± 0.36 |

It has been confirmed that those change in Penh value has been prominent in case of higher-dose methacholine treatment group rather than in lower-dose methacholine treatment group and the Penh value in the test sample for the same concentration of methacholine, has been remarkably decreased in a dose dependent manner.

Accordingly, it has been confirmed that the inventive purified extract effectively suppressed the airway hyperresponsiveness and therefore, they are useful in treating or preventing the asthma disease, an allergic disease in airway.

Experimental Example 3. Effect on the Level of Eosinophil and Inflammatory Cells in BALF In order to confirm the inhibition effect of test samples prepared in Examples on the level of eosinophil and inflammatory cells in bronchoalveolar fluid (BALF), following test was performed by the method disclosed in the literature (Chen M. et al., *Immunolgy*, pp 376-384, 2011).

The bronchoalveolar lavage fluid (BALF) prepared in Experimental Example 1 was recovered to determine the level of inflammatory cells.

The total inflammatory cell number was assessed by the counting of cells in at least five squares of a hemocytometer after excluding dead cells by staining with trypan blue (Daigle I. et al., *Swiss Med Wkly*, 131, pp 231-7, 2001). 1000 of BALF was loaded onto a slide and centrifuged (200×g, 4° C., 10 min) to fix the cells onto the slide using a Cellspin machine (Cyto12.5+clip5, Hanil Science Industrial, Korea). The cells were stained by Diff-Quick® Stain reagents (Sysmex, Cat No. 38721, Switzerland) according to the manufacturer's instructions. Statistical significance was determined by Student's two-tailed t-test for independent means and the critical level for significance was set at $P<0.05$.

Figure 5:
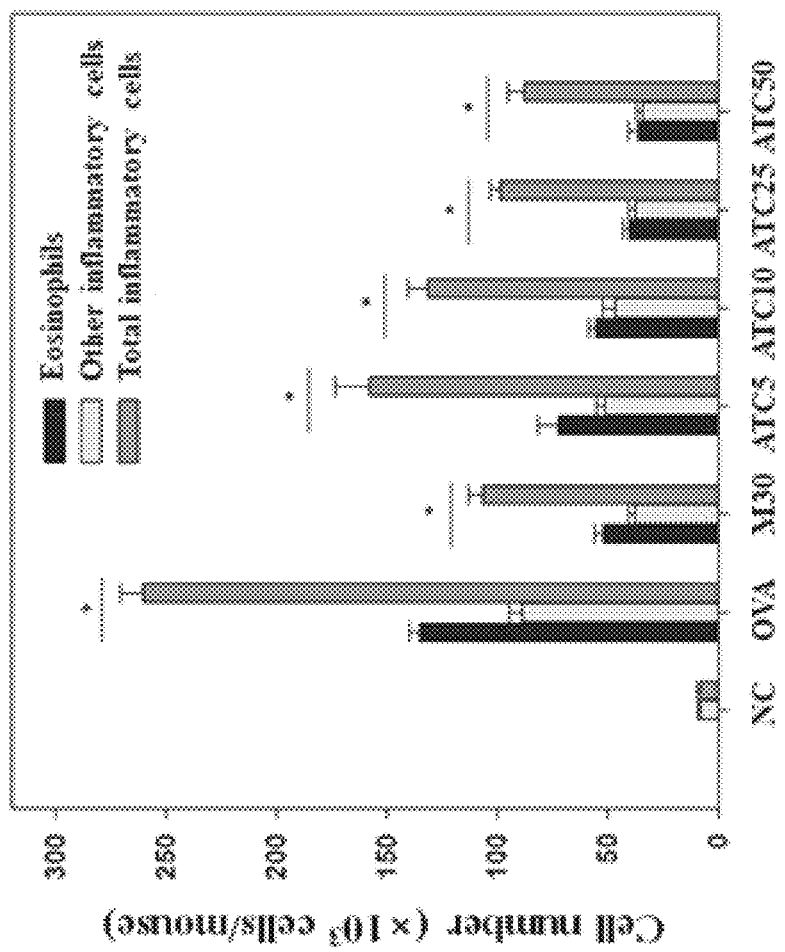
FIG. 5 shows the inhibitory effect of the inventive purified extract on the recruitment of inflammatory cells in bronchoalveolar lavage fluid.

As shown in FIG. 5, the total number of eosinophil and inflammatory cells in the control group treated and inhaled with OVA as an asthma induced group (OVA) was significantly increased comparing with those in the non-treatment group with OVA as a normal control group (NC).

The total number of eosinophil and inflammatory cells in the positive control group treated with Montelukast (MO) as well as the test sample group orally administered with various concentrations of test samples (ATC-5, ATC-10, ATC-25, and ATC-50) were significantly reduced. (See Table 7)

TABLE 7

| total number of eosinophil and inflammatory cells in BALF | | | |
|---|---|---|---|
| | | No. of inflammatory cells ($10^3$ cells/mouse) | |
| | | No. of eosinolphil | No. of inflammatory cells |
| NC | | 0.00 ± 0.00 | 8.28 ± 1.46 |
| OVA | | 135.44 ± 4.54 | 260.48 ± 10.39 |
| ATC2 | 5 | 72.23 ± 9.45 | 158.2 ± 15.38 |
| (mg/kg) | 10 | 55.40 ± 3.46 | 131.67 ± 9.03 |
| | 25 | 40.8 ± 2.34 | 98.6 ± 4.57 |
| | 50 | 36.57 ± 4.02 | 88.1 ± 7.04 |
| M30 | | 52.03 ± 4.06 | 106.67 ± 6.48 |

Experimental Example 4. Effect on the Level of IgE and OVA-Specific IgE in Blood Serum In order to confirm the inhibition effect of test samples prepared in Examples on the level of IgE and OVA-specific IgE in blood serum, following test was performed by the method disclosed in the literature (Kay, A. B., *The New England Journal of Medicine*, 344, pp 30-37, 2001).

The blood serum and bronchoalveolar lavage fluid (BALF) prepared in Experimental Example 1 was recovered to determine the level of IgE and OVA-specific IgE in blood serum.

The blood serum and bronchoalveolar lavage fluid (BALF) was added to 96-well plates (ELISA plate) and coated with 0.1M $NaHCO_3$ buffer solution (pH 8.3) containing 20 μg/ml of OVA (Sigma, MO, USA) at 4° C. overnight. After inhibiting nonspecific reaction using by PBS containing 1% bovine serum albumin, the serum for testing was diluted to 1:400 and reacted together for 2 hours at room temperature. After washing, the serum was reacted with diluted (×300) anti-mouse IgE monoclonal antibody (MCA419, Serotec, Oxford, UK) for 2 hours and with diluted (×4000) HRP-conjugated goat anti-rat IgG polyclonal A (STAR110P, Serotec, UK) for 1 hours at room temperature. After washing, the solution was stained with 3,3', 5,5'-tetramethylbenzidine (52-00-02, KPL) substrate and the reaction was stopped by 2N $H_2SO_4$ to determine the absorbance using by spectroscopy (Versamax, Molecular Devices, US) at 450 nm.

Figure 6:
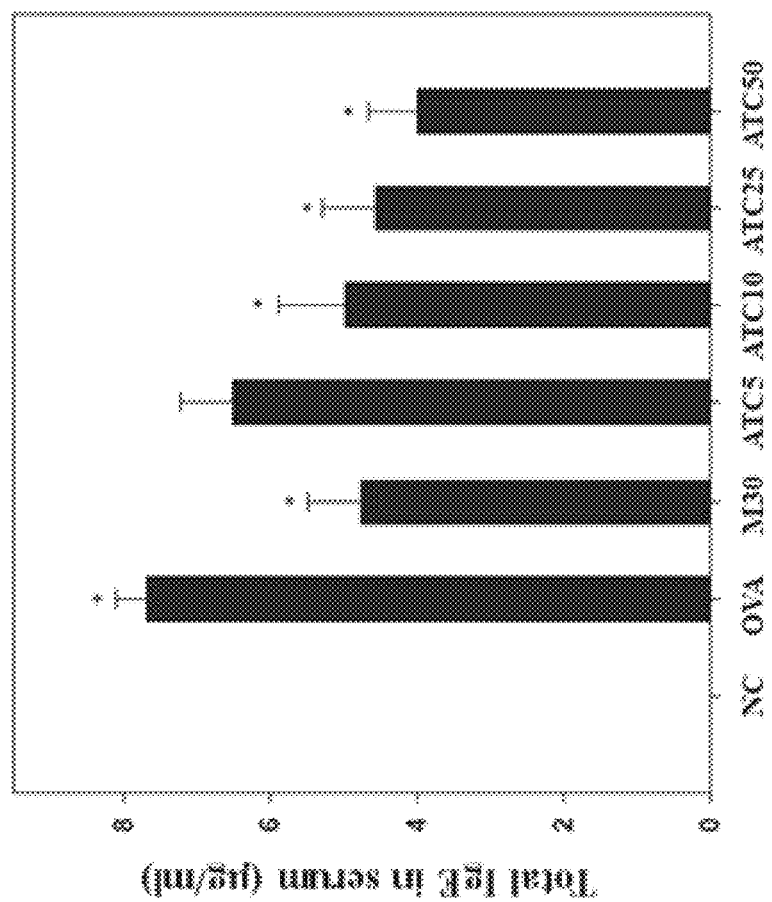
FIG. 6 shows the inhibitory effect of the inventive purified extract on the release of immunoglobulin (total IgE) in blood serum.
Figure 7:
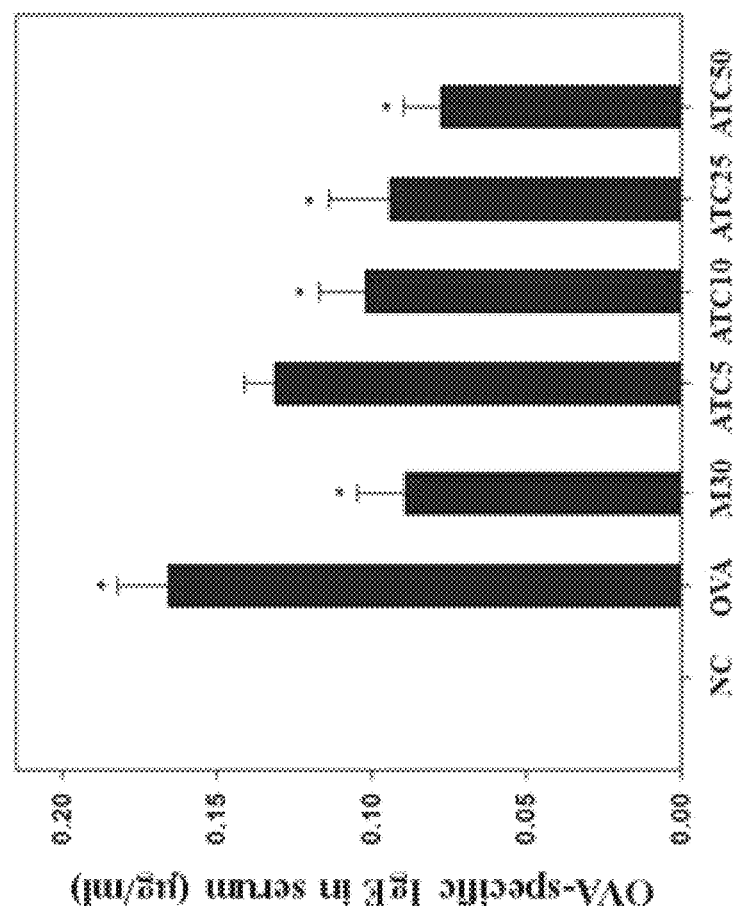
FIG. 7 shows the inhibitory effect of the inventive purified extract on the release of OVA-specific IgE in blood serum.

As shown in FIG. 6 and FIG. 7, the level of IgE and OVA-specific IgE in blood serum in the control group treated and inhaled with OVA as an asthma induced group (OVA) was significantly increased whereas those in the positive control group treated with Montelukast (MO) as well as the test sample group orally administered with various concentrations of test samples (ATC-5, ATC-10, ATC-25, and ATC-50) were significantly reduced. (See Table 8)

TABLE 8

The level of IgE and OVA-specific IgE in blood serum

| | | Concentration (µg/ml) | |
|---|---|---|---|
| | | level of IgE in serum | level of OVA-specific IgE |
| NC | | 0.92 ± 0.17 | 0.05 ± 0.00 |
| OVA | | 7.68 ± 0.42 | 0.17 ± 0.02 |
| ATC2 | 5 | 6.51 ± 0.72 | 0.13 ± 0.01 |
| (mg/kg) | 10 | 4.97 ± 0.91 | 0.10 ± 0.01 |
| | 25 | 4.56 ± 0.73 | 0.09 ± 0.02 |
| | 50 | 4.01 ± 0.67 | 0.08 ± 0.01 |
| M30 | | 4.76 ± 0.73 | 0.09 ± 0.02 |

Accordingly, it has been confirmed that the inventive purified extract effectively inhibited the level of IgE and OVA-specific IgE in blood serum and therefore, they are useful in treating or preventing the allergic disease and asthma disease.

Experimental Example 5. Effect on the Level of Inflammatory Cytokines in BALF

In order to confirm the inhibition effect of test samples prepared in Examples on the level of Th2 cytokines (IL-4, IL-5 and IL-13) and IL-1β in bronchoalveolar lavage fluid (BALF), following test was performed by the sandwich enzyme immunosorbent assay method disclosed in the literature (Renz H. et al., *J. Exp. Med.*, 1777, pp 1175-1180, 1993).

The blood serum and bronchoalveolar lavage fluid (BALF) was added to 96-well plates (ELISA plate) coated with cytokine antibody to induce antigen-antibody reaction for 2 hours at room temperature. The level of Th2 cytokines (IL-4, IL-5 and IL-13) and IL-1β in bronchoalveolar lavage fluid (BALF) was determined using by ELISA kit (Biosource Int. CA, USA) specifically reacting with each cytokine according to the manufacture's manual.

Figure 8:
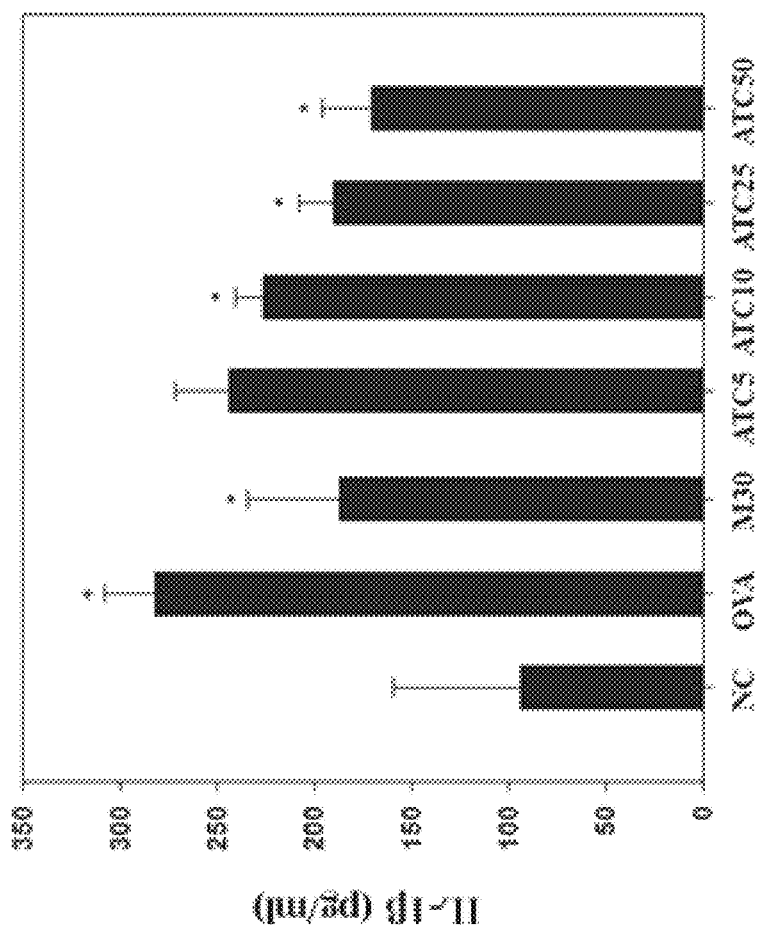
FIG. 8 represents the inhibitory effect of the inventive purified extract on the release of IL-1 beta.
Figure 9:
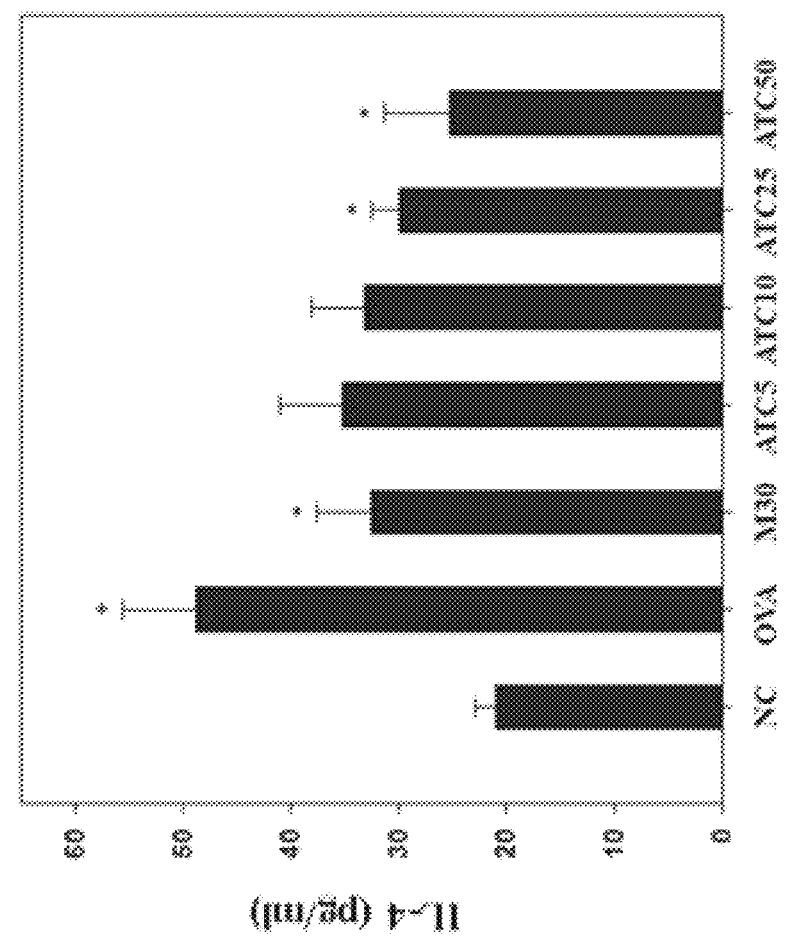
FIG. 9 presents the inhibitory effect of the inventive purified extract on the release of inflammatory chemokines.

As shown in FIG. 8 and FIG. 9, 48 hours after the OVA-treatment, the level of Th2 cytokines (IL-4, IL-5 and IL-13) and IL-1β in the control group treated and inhaled with OVA as an asthma induced group (OVA) was significantly increased comparing with those in the non-treatment group with OVA as a normal control group (NC).

The increased level of Th2 cytokines (IL-4, IL-5 and IL-13) and IL-1β in the positive control group treated with Montelukast (MO, 30 mg/kg) as well as the test sample group orally administrated with various concentrations of test samples (ATC-10, ATC-25, and ATC-50) were significantly reduced. (See Table 9)

TABLE 9

The level of Th2 cytokines (IL-4, IL-5 and IL-13) and IL-1β

| | | conc. (pg/ml) | | | |
|---|---|---|---|---|---|
| | | IL-1β | IL-4 | IL-5 | IL-13 |
| NC | | 94.12 ± 65.24 | 20.94 ± 1.76 | 57.51 ± 3.15 | 22.25 ± 3.04 |
| OVA | | 281.78 ± 26.15 | 48.76 ± 6.96 | 109.48 ± 2.87 | 44.76 ± 4.85 |
| ATC2 | 5 | 243.93 ± 27.58 | 35.27 ± 5.26 | 90.77 ± 12.78 | 34.29 ± 7.55 |
| (mg/kg) | 10 | 226.33 ± 14.21 | 35.18 ± 4.45 | 79.26 ± 9.60 | 29.50 ± 2.76 |
| | 25 | 190.30 ± 17.82 | 29.94 ± 2.32 | 73.74 ± 9.54 | 27.27 ± 4.42 |
| | 50 | 170.70 ± 25.43 | 25.26 ± 5.55 | 57.92 ± 19.99 | 23.53 ± 4.10 |
| M30 | | 187.03 ± 47.17 | 32.60 ± 4.53 | 69.74 ± 7.17 | 25.93 ± 4.13 |

Accordingly, it has been confirmed that the inventive purified extract effectively inhibited the level of level of Th2 cytokines (IL-4, IL-5 and IL-13) and IL-1β in BALF and therefore, they are useful in treating or preventing the allergic disease and asthma disease.

Experimental Example 6. Lung Histology

In order to confirm the anti-asthmatic effect of test samples prepared in Examples, following histopathological analysis on broncho-alveolar tissue was performed by the method disclosed in the literature (Kwak Y G. et al., *J. Clin. Invest.*, 111, pp 1083-1092, 2003).

The delivered lung tissues of BALB/c mice which had not perform broncho-alveolar lavage was fixed for 24 h in 10% neutral-buffered formalin. After being embedded in paraffin, then made into 4-µm thickness sections, the tissue was stained with H&E solution (hematoxylin; Sigma MHS-16 and eosin, Sigma HT110-I-32) and the inflammation score of five regions in each section chosen in a randomized manner, was determined. (Inflammation score 0: inflamed cells is not found in bronchial surrounding, Inflammation score 1: inflamed cells is sporadically found in bronchial surrounding, Inflammation score 2: thin inflamed cell layer is found in most of bronchial surrounding, Inflammation score 3: thick inflamed cell layer is found in most of bronchial surrounding).

Figure 10:
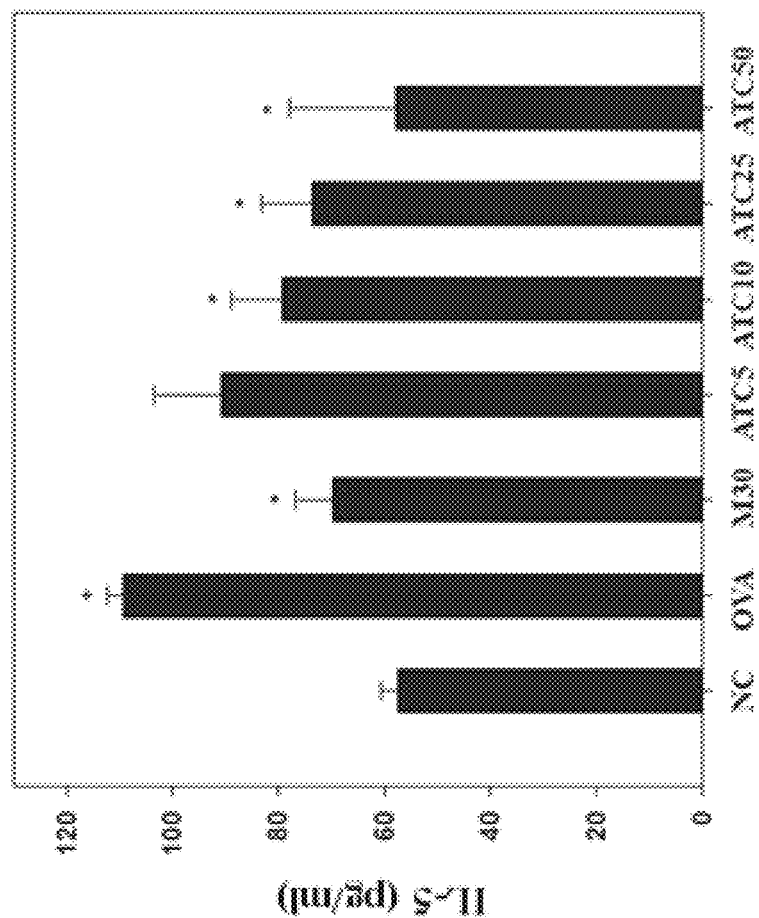
FIG. 10 represents the inhibitory effect of the inventive purified extract on the recruitment of inflammatory cells on lung tissue cell using by the histological examination of bronchoalveolar lavage.

As shown in FIG. 10, many inflammatory cells including eosinophills were found in bronchiolar surroundings and hyperplasia of epithelial cells as well as hypertrophy of tracheal muscle were also found in the control group treated and inhaled with OVA as an asthma induced group (OVA) whereas the invasion of the inflamed cells was significantly reduced in the positive control group treated with Montelukast (MO, 30 mg/kg) as well as the test sample group orally administrated with various concentrations of test samples (ATC-10, ATC-25, and ATC-50). (See Table 10)

TABLE 10

Inflammation score and the ratio of goblet cell in bronchiolar epithelial cell

| | | histopathological analysis | |
|---|---|---|---|
| | | Inflammation score | PAS + cells/bronchiole (%) |
| NC | | 0.06 ± 0.05 | 2.19 ± 0.54 |
| OVA | | 2.11 ± 0.07 | 52.75 ± 1.42 |
| ATC2 (mg/kg) | 5 | 1.75 ± 0.17 | 48.07 ± 1.15 |
| | 10 | 1.33 ± 0.14 | 44.59 ± 1.60 |
| | 25 | 1.17 ± 0.11 | 38.61 ± 1.74 |
| | 50 | 1.08 ± 0.18 | 35.71 ± 1.14 |
| M30 | | 1.25 ± 0.13 | 39.21 ± 2.34 |

Experimental Example 7. Evaluation of Goblet Cell Plasia

In order to confirm the anti-asthmatic effect of test samples prepared in Examples, following goblet cell plasia analysis on broncho-alveolar tissue was performed by the method disclosed in the literature (Lee K S. et al., *FASEB J.*, 20, pp 455-465, 2006).

Figure 11:
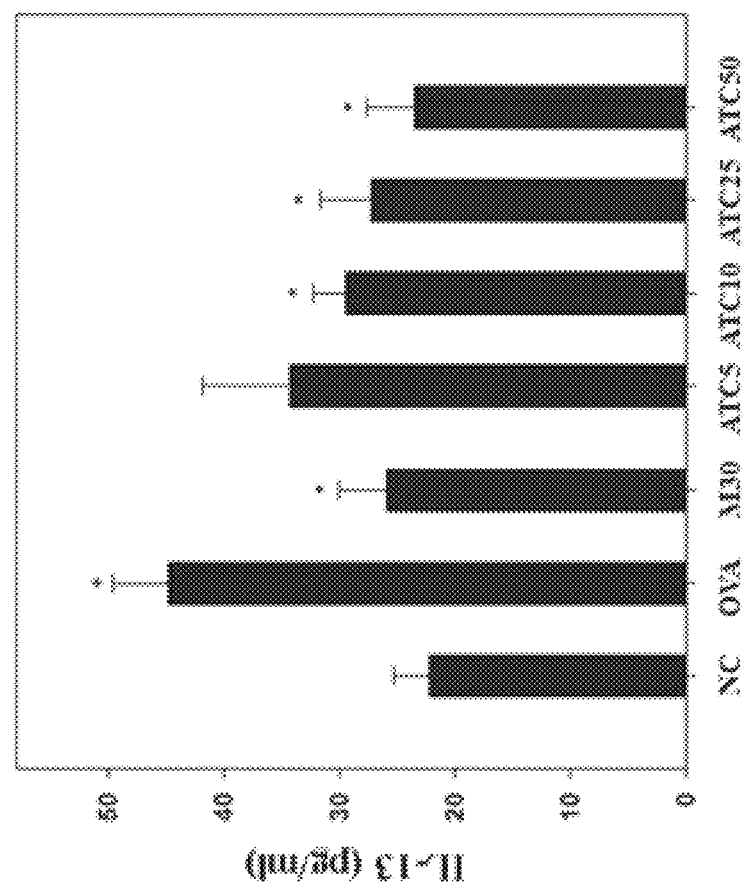
FIG. 11 represents the inhibitory effect of the inventive purified extract on the mucus secretion in lung tissue cell using by the histological examination of bronchoalveolar lavage.
Figure 12:
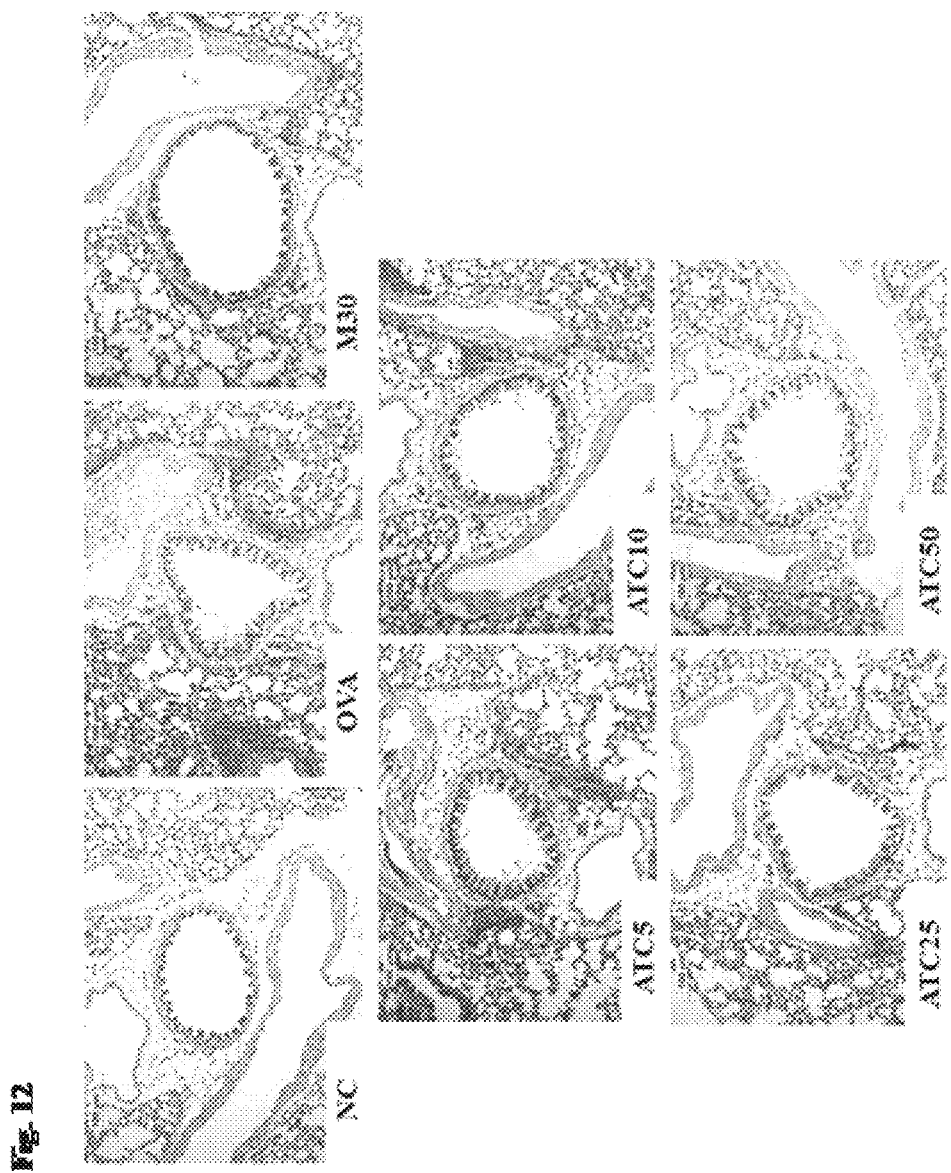
FIGS. 12 and 13 represent the inhibitory effect of the inventive purified extract on the recruitment of inflammatory cells on lung tissue cell using by the histological examination of bronchoalveolar lavage.
Figure 13:
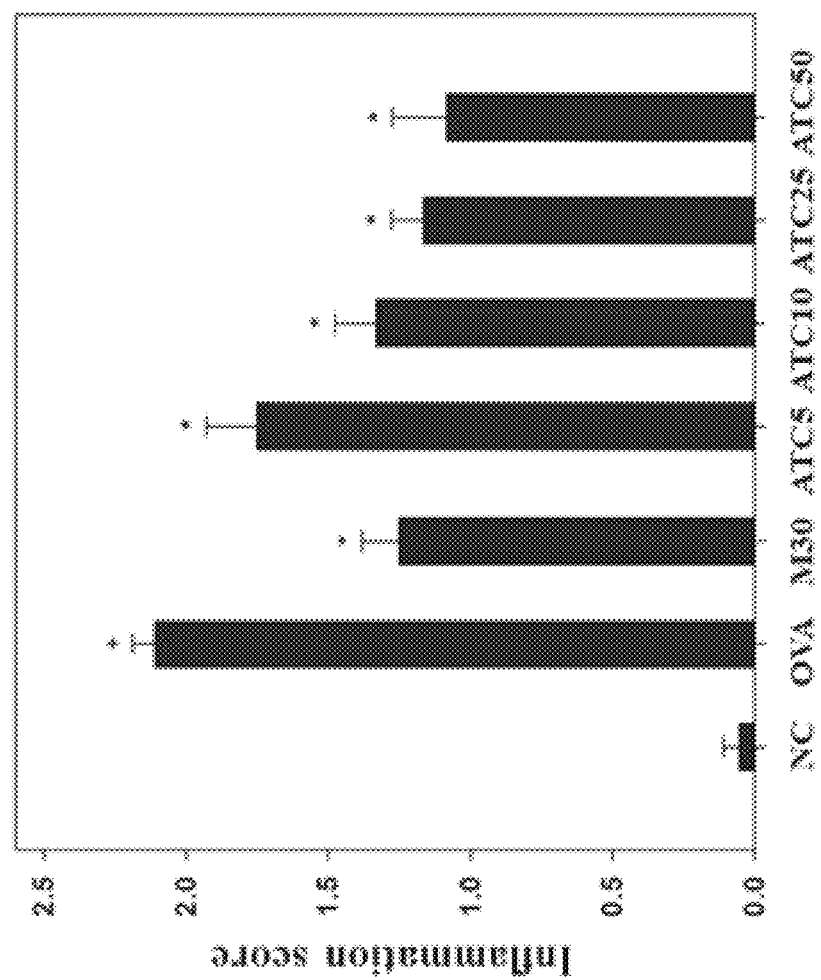
Figure 14:
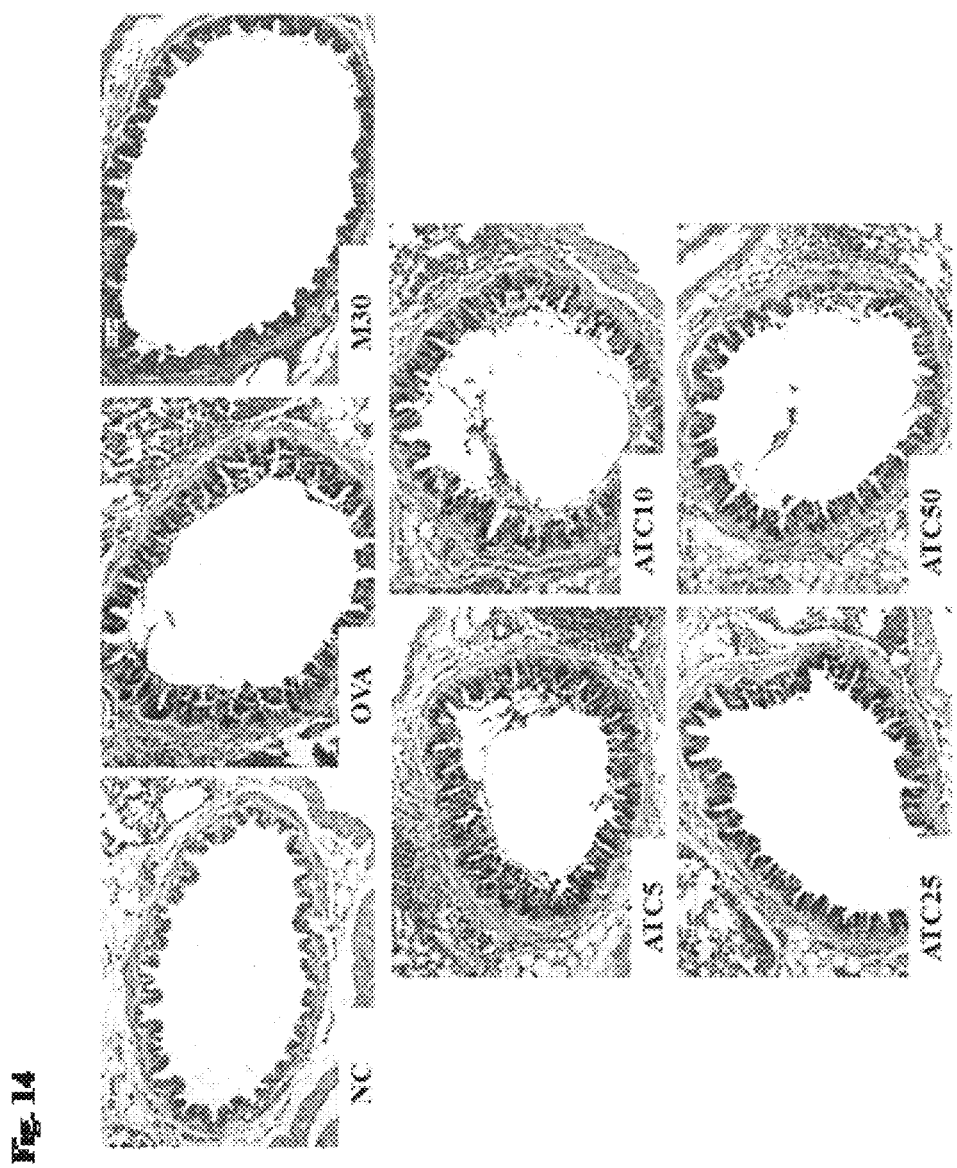
FIGS. 14 and 15 represents the inhibitory effect of the inventive purified extract on the mucus secretion in lung tissue cell using by the histological examination of bronchoalveolar lavage.
Figure 15:
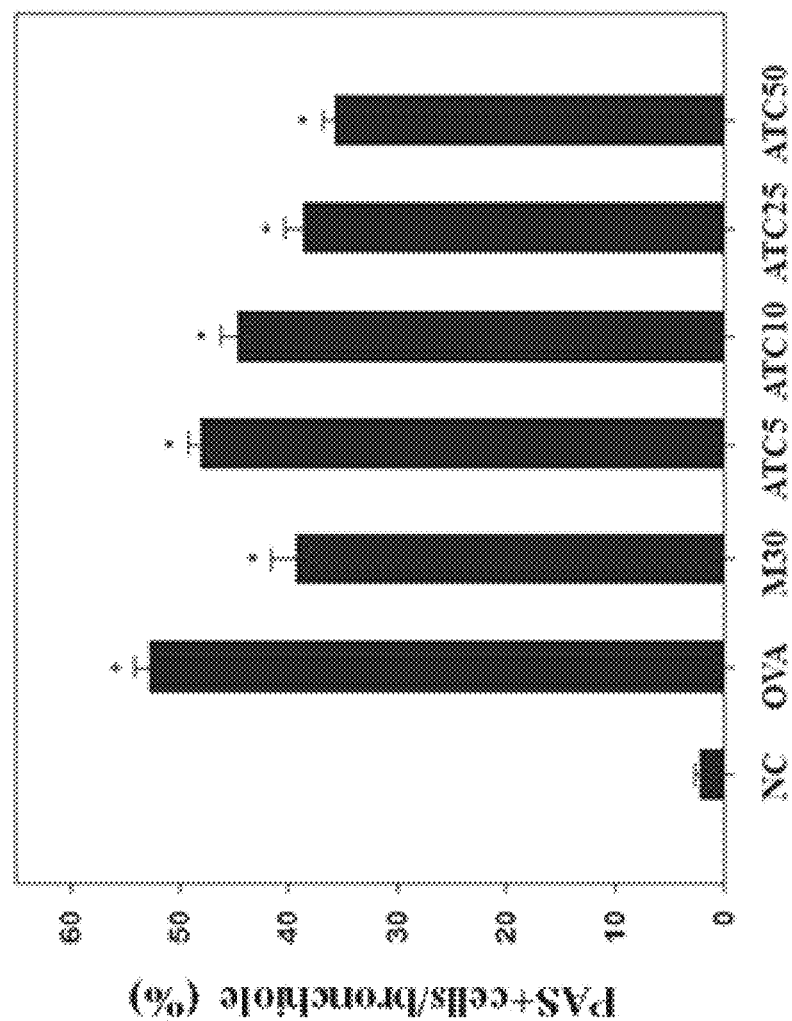

The delivered lung tissues of BALB/c mice which had not perform broncho-alveolar lavage was fixed for 24 h in 10% neutral-buffered formalin. After being embedded in paraffin, then made into 4-μm thickness sections, the tissue was stained with Periodic acid Schiff (PAS stain kit, T-K7308, IMEB, CA, USA) to determine the ratio of goblet cell in bronchiolar epithelial cell As shown in FIG. 11, the ratio of goblet cell in bronchiolar epithelial cell was significantly increased in the control group treated and inhaled with OVA as an asthma induced group (OVA) comparing with normal control group (Nc) whereas the ratio of goblet cell in bronchiolar epithelial cell was significantly reduced in the positive control group treated with Montelukast (MO, 30 mg/kg) as well as the test sample group orally administrated with various concentrations of test samples (ATC-10, ATC-25, and ATC-50). (See Table 9)

Experimental Example 8. Acute Toxicity Test of Oral Administration in Rat

The acute toxicity test was performed by administrating inventive extract to 6-weeks aged SPF Sprague-Dawley rats.

250 mg/kg, 500 mg/kg, 1000 mg/kg, 5000 mg/kg of inventive extract was orally administrated to each group consisting of 2 rats and the symptoms of rats were observed for 14 days. After administrating the extract or compounds, all the clinical changes i.e., mortality, clinical signs, body weight changes was observed and blood test such as haematological test and hematological biochemistry test was performed. The abnormal changes of abdominal organ and thoracic organ were observed after autopsy.

There did not show any changes in mortality, clinical signs, body weight changes and gross findings in any group or either gender. Furthermore, there showed any toxicity in test group treated with 5000 mg/kg of inventive extract or compounds.

Accordingly, it has been confirmed that the inventive extract prepared in the present invention was potent and safe substance showing $LD_{50}$ (more than 5000 mg/kg) in oral administration.

MODE FOR INVENTION

Hereinafter, the formulating methods and kinds of excipients will be described, but the present invention is not limited to them. The representative preparation examples were described as follows.
Preparation of Injection
ATC1 extract 100 mg
Sodium metabisulfite 3.0 mg
Methyl paraben 0.8 mg
Propyl paraben 0.1 mg
Distilled water for injection optimum amount
 Injection preparation was prepared by dissolving active component, controlling pH to about 7.5 and then filling all the components in 2 Ml ample and sterilizing by conventional injection preparation method.
Preparation of Powder
ATC2 extract 500 mg
Corn Starch 100 mg
Lactose 100 mg
Talc 10 mg
 Powder preparation was prepared by mixing above components and filling sealed package.
Preparation of Tablet
ATC1 extract 200 mg
Corn Starch 100 mg
Lactose 100 mg
Magnesium stearate optimum amount
 Tablet preparation was prepared by mixing above components and entabletting.
Preparation of Capsule
ATC2 extract 100 mg
Lactose 50 mg
Corn starch 50 mg
Talc 2 mg
Magnesium stearate optimum amount
 Tablet preparation was prepared by mixing above components and filling gelatin capsule by conventional gelatin preparation method.
Preparation of Liquid
ATC1 extract 1000 mg
Sugar 20 g
Polysaccharide 20 g
Lemon flavor 20 g
 Liquid preparation was prepared by dissolving active component, and then filling all the components in 1000 Ml ample and sterilizing by conventional liquid preparation method.
Preparation of Health Food
ATC2 extract 1000 mg
Vitamin mixture optimum amount
Vitamin A acetate 70 g
Vitamin E 1.0 mg
Vitamin $B_{10}$. 13 mg
Vitamin $B_2$ 0.15 mg
Vitamin B6 0.5 mg
Vitamin B1 20.2 g
Vitamin C 10 mg
Biotin 10 g
Amide nicotinic acid 1.7 mg
Folic acid 50 g
Calcium pantothenic acid 0.5 mg
Mineral mixture optimum amount
Ferrous sulfate 1.75 mg
Zinc oxide 0.82 mg
Magnesium carbonate 25.3 mg
Monopotassium phosphate 15 mg Dicalcium phosphate 55 mg
Potassium citrate 90 mg
Calcium carbonate 100 mg
Magnesium chloride 24.8 mg The above mentioned vitamin and mineral mixture may be varied in many ways. Such variations are not to be regarded as a departure from the spirit and scope of the present invention.

Preparation of Health Beverage
ATC1 extract 1000 mg
Citric acid 1000 mg
Oligosaccharide 100 g
Apricot concentration 2 g
Taurine 1 g
Distilled water 900 Ml Health beverage preparation was prepared by dissolving active component, mixing, stirred at 85° C. for 1 hour, filtered and then filling all the components in 1000 Ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the present invention provides inventive novel industrialized method for preparing purified extract containing more abundant active ingredients such as catalpol derivatives from the extract of *Pseudolysimachion rotundum* var *subintegrum* and the purified extract showed more potent anti-inflammatory, anti-allergy and anti-asthma activity than that prepared by the conventional preparation method disclosed in the prior art through various in vivo tests such as inhibition test on the reproduction of eosinophil, the release of immunoglobulin and inflammatory chemokines in plasma and bronchoalveolar fluid as well as the suppression of airway hyperresponsiveness and goblet cell hyperplasia in a OVA-sensitized/challenged mouse model. Therefore, it can be used as the therapeutics or functional health food for treating and preventing inflammatory, allergic or asthmatic disease.

The invention claimed is:

1. A method of treatment comprising the administering of the pharmaceutical composition comprising a purified extract fractionated with butanol (ATC1) from the extract of *Pseudolysimachion rotundum* var *subintegrum*, comprising 15%-50% (w/w) verproside, 0.3%-10% (w/w) veratric acid, 0.5%-10% (w/w) catalposide, 0.3%-10% (w/w) picroside II, 0.3%-10% (w/w) isovanilloyl catalpol and 0.5%-10% (w/w) 6-O-veratroyl catalpol based on the weight of total extract (100%) of *Pseudolysimachion rotundum* var *subintegrum* to a subject in need of treatment of an ailment selected from the group consisting of an inflammatory disease, an allergy disease and an asthma disease.

2. A method of treatment comprising the administering of the pharmaceutical composition comprising a purified extract fractionated with butanol (ATC1) from the extract of *Pseudolysimachion rotundum* var *subintegrum*, comprising 12.3%-47% (w/w) catalpol derivatives selected from the group consisting of verproside, catalposide, picroside II, isovanilloyl catalpol and 6-O-veratroyl catalpol in total extract (100%) of *Pseudolysimachion rotundum* var *subintegrum* and which has a relative mixed ratio (w/w) between weight of each catalpol derivative of 15.0-18.0 (w/w) verproside, 2.10-2.60 (w/w) catalposide, 1 (w/w) picroside II, 1.00-1.30 (w/w) isovanilloyl catalpol and 2.00-2.30 (w/w) 6-O-veratroyl catalpol to a subject in need of treatment of an ailment selected from the group consisting of an inflammatory disease, an allergy disease and an asthma disease.

3. The method of claim 1,
wherein the inflammatory disease is selected from the group consisting of eczema, atopic dermatitis, conjunctivitis, periodontal disease, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, systemic lupus erythematosus, fibromyalgia, psoriatic arthritis, osteoarthritis, rheumatic arthritis, periarthritis of shoulder, tendinitis, tenosynovitis, peritendinitis, myositis, hepatitis, cystitis, nephritis, Sjogren's syndrome, multiple sclerosis, chronic inflammatory disease, and acute inflammatory disease;
wherein the allergy disease is selected from the group consisting of allergic rhinitis, allergic dermatitis, contact dermatitis, hives, insect allergy, food allergy, drug allergy, allergic conjunctivitis, and hypersensitivity; and
wherein the asthma disease is selected from the group consisting of sensitivity to dust mites, fur, dandruff, cockroach, food, drug, cough, cigarette smoke, air pollution, food additive, physical activity, exercise, weather change, yellow sand and stress.

4. The method of claim 2,
wherein the inflammatory disease is selected from the group consisting of eczema, atopic dermatitis, conjunctivitis, periodontal disease, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, systemic lupus erythematosus, fibromyalgia, psoriatic arthritis, osteoarthritis, rheumatic arthritis, periarthritis of shoulder, tendinitis, tenosynovitis, peritendinitis, myositis, hepatitis, cystitis, nephritis, Sjogren's syndrome, multiple sclerosis, chronic inflammatory disease, and acute inflammatory disease;
wherein the allergy disease is selected from the group consisting of allergic rhinitis, allergic dermatitis, contact dermatitis, hives, insect allergy, food allergy, drug allergy, allergic conjunctivitis, and hypersensitivity; and
wherein the asthma disease is selected from the group consisting of sensitivity to dust mites, fur, dandruff, cockroach, food, drug, cough, cigarette smoke, air pollution, food additive, physical activity, exercise, weather change, yellow sand and stress.

* * * * *